Figure 1A:
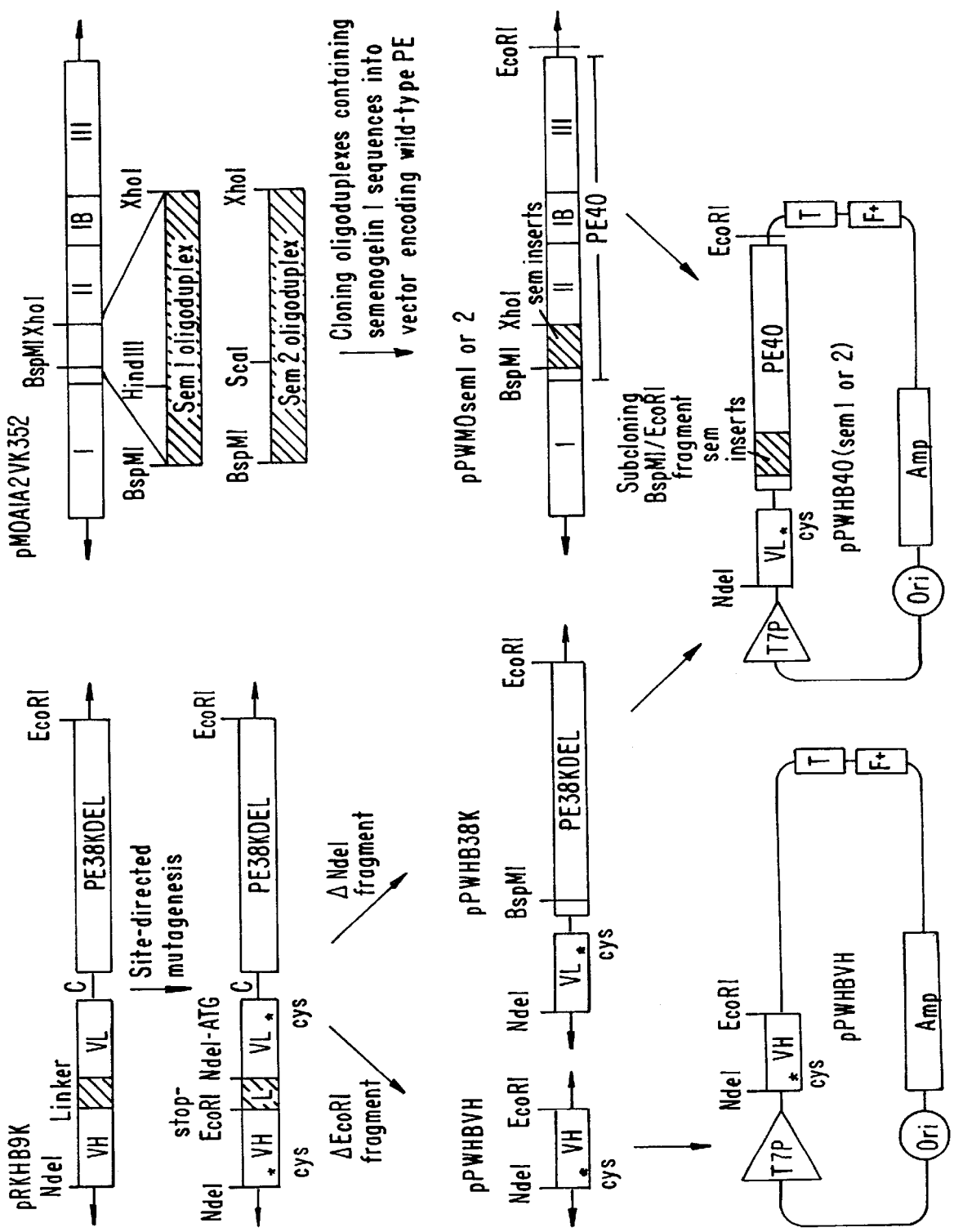

United States Patent
Fitzgerald et al.

(10) Patent No.: US 6,426,075 B1
(45) Date of Patent: Jul. 30, 2002

(54) PROTEASE-ACTIVATABLE PSEUDOMONAS EXOTOXIN A-LIKE PROPROTEINS

(75) Inventors: **

U.S. PATENT DOCUMENTS

| | | |
|---|---|---|
| 5,696,237 A | 12/1997 | FitzGerald et al. |
| 5,705,156 A | 1/1998 | Pastan et al. |
| 5,705,163 A | 1/1998 | Pastan et al. |
| 5,854,044 A | 12/1998 | Pastan et al. |
| 5,863,745 A | 1/1999 | FitzGerald et al. |

OTHER PUBLICATIONS

Gray et al; Cloning, Nucleotide Sequence and Expresion in *Escherichia coli* of Exotoxin A Structural Gene of *Pseudomonas aeruginosa*; Proc.Natl.Acad.Sci; 81;2645–2649, 1984.*

Schafer et al. "Two Independent targeting signals in the cytoplasmic domain determine trans–Golgi network localization and endosomal trafficking of the proprotien convertase furin," *EMBO J.* 14(11): 2424–35 (1995).

Allured et al. "Structure of exotoxin A of *Pseudomonas aeruginosa* at 3.0–Angstrom resolution," *Proc. Natl. Acad. Sci.* 83:1320–1324 (1986).

Gordon et al. "Proteolytic activation of bacterial toxins by eukaryotic cells is performed by furin and by additional cellular proteases," *Infection and Immunity* 63(1):82–87 (1995).

Pastan et al. "Recombinant toxins for cancer treatment," *Science* 254:1173–1177 (1991).

Pastan et al. "Pseudomonas exotoxin: Chimeric toxins," *J. of Biol. Chem.* 264(26):15157–15160 (1989).

Denmeade et al. "Specific and efficient peptide substrates for assaying the proteolytic activity of prostate–specific antigen," *Cancer Research* 57:4924–4930 (1997).

* cited by examiner

| Plasmid | Protein | Immunotoxin | Structure |
|---|---|---|---|
| pPWHBVH<br>pPWHB40 | HB21VH(cys)<br>HB21VL(CYS)PE40 | HB21dsFvPE40(wt) | Furin cleavage site<br>253 279 365 400 613<br>VL — I — I8 — III<br>S–S<br>VH |
| pPWHBVH<br>pPWHB40(sem1) | HB21VH(cys)<br>HB21VL(CYS)PE40(sem1) | HB21dsFvPE40(sem1) | PSA cleavage site<br>VL–sem1 — I — I8 — III<br>S–S<br>VH |
| pPWHBVH<br>pPWHB40(sem2) | HB21VH(cys)<br>HB21VL(CYS)PE40(sem2) | HB21dsFvPE40(sem2) | PSA cleavage site<br>VL–sem2 — I — I8 — III<br>S–S<br>VH |

FIG. 1B.

A

B

IMMUNOTOXIN HB21dsFvPE40

Cleavage of three variants by the proteases furin and urokinase (uPA)

| | (aa 272-284)* | Furin | uPA |
|---|---|---|---|
| Location → | P P<br>4321 ↙ cleavage | | |
| wtPE | FTRHRQPR GWEQL | ++ | - |
| DT8 | ↙ cleavage<br>FACNRVRR SVGQL | ++++ | +++ |
| DT8ala276 | ↙ cleavage<br>FACNAVRR SVGQL | - | ++ |

FIG. 7.

PROTEASE-ACTIVATABLE PSEUDOMONAS EXOTOXIN A-LIKE PROPROTEINS

This application claims the benefit of the filing date of U.S. provisional patent application serial No. 60/030,376, filed Nov. 6, 1996, incorporated herein in its entirety by reference.

TECHNICAL FIELD

Methods and compositions relating to Pseudomonas exotoxin proproteins modified for selective toxicity. The exotoxin is modified to be activated by a desired protease by insertion of a protease activatable sequence in the domain II loop. Activation of the proprotein results in formation of the cytotoxic Pseudomonas exotoxin.

BACKGROUND OF THE INVENTION

Pseudomonas Exotoxin (PE), which binds and enters mammalian cells by receptor-mediated endocytosis, depends on proteolytic cleavage to generate a C-terminal active fragment which translocates to the cell cytosol, ADP-ribosylates elongation factor 2 and inhibits protein synthesis. Mutant versions of PE which cannot be processed appropriately by cells are non-toxic. Furin has been identified as the intracellular protease responsible for this cleavage. Cleavage occurs between arginine 279 and glycine 280 in an arginine-rich loop located in domain II of the toxin. In biochemical experiments, furin-mediated cleavage is evident only under mildly acidic conditions (pH 5.5). Recently, Garten et al., (*EMBO J*, 14(11):2424–35 (1995)) have proposed that sequences in the cytoplasmic tail of furin are responsible for its cycling to the cell surface and re-entry through the endosomal compartment. Since PE enters cells via the alpha 2-macroglobulin receptor/Low density lipoprotein receptor-related protein (LRP), it is likely that this receptor delivers PE to an acidic endosomal compartment where it is cleaved by furin. PE is broadly cytotoxic because most mammalian cells and tissues express both LRP and furin. In vivo, the injection of native PE produces profound liver toxicity.

PE has been crystallized and its three dimensional structure determined by X-ray diffraction analysis (Allured et al., *Proc. Natl. Acad. Sci.*, 83:1320–1324 (1986)). PE comprises four structural domains: the N-terminal domain (domain Ia) mediates binding to LRP, a second domain (domain II) has the protease processing site and sequences necessary for translocation to the cytosol; a third domain (domain Ib) has no identified function; and a fourth, C-terminal domain (domain III), has ADP-ribosylating activity and an ER retention sequence.

The existing strategy for targeting the cell-killing activity of PE to cancer cells is to delete the DNA encoding the cell binding domain and replace it with cDNAs encoding binding ligands or antibody fragments that recognize cancer-related cell surface determinants. Surface binding then mediates the internalization of PE-immunotoxins to a furin-containing compartment where the appropriate C-terminal fragment is generated. Since most cancer cells express furin, this cleavage-activation step does not contribute to the selectivity of immunotoxin action.

Data from Phase I/III clinical trials indicate that the low level expression of target antigens on normal cells represents a significant impediment to the success of immunotoxin-based therapeutics. This problem may be particularly relevant for the treatment of solid tumors, where individual cancer cells are difficult to access and high levels of immunotoxins must be maintained for prolonged periods.

Cancer cells frequently express high levels of certain proteases including metalloproteinases, serine proteases and various lysosomal enzymes. These function both to promote metastatic spread of cells and to release (from precursors and binding proteins) growth factors locally. Prostate specific antigen (PSA), is a kallikrein-like protease which normally cleaves Semenogelin I and II at several sites but is often elevated to very high levels in patients with prostate cancer. Further, several recent reports suggest that PSA is also expressed in breast cancer tissue. In prostate cancer, PSA is found circulating in serum as a complex with CTI but apparently is active locally where it confers some survival advantage to prostate cancer cells by virtue of its ability to degrade matrix proteins and release insulin-like growth factor from its binding proteins.

SUMMARY OF THE INVENTION

Pseudomonas Exotoxin A ("PE") is translocated into the cytosol after a furin recognition site in domain II is cleaved by furin. Protease-activatable PE-like proproteins are engineered to replace the furin recognition site by a site recognized by a protease made or secreted by a cell targeted for death, for example, a cancer cell. Upon cleavage by the target protease, the PE-like proprotein is translocated into the cytosol where the toxin's ADP-ribosylating activity kills the cell by interfering with polypeptide elongation.

The PE-like proproteins of this invention offer several advantages. First, because they are activated by a target protease, and not by furin, their toxicity is significantly more cell-specific than native PE. Second, when the cysteine-cysteine loop of PE domain II is cleaved, the disulfide bond, before it is reduced, holds the cell-recognition domain attached to the rest of PE. Many cancer cells secrete cell-specific proteases that tend to accumulate around the cell. For example, prostate cancer cells secrete prostate specific antigen. Therefore, the proproteins of this invention may be cleaved before entering the target-cell. However, the protease activatable sequence is introduced into the cysteine-cysteine loop of a domain II-like sequence of the proprotein. Therefore, the cell recognition domain is still attached upon cleavage of the proprotein outside the cell, and still is available to bind to a cell surface receptor for subsequent endocytosis. Third, by selecting a proper cell recognition domain, the toxins can be targeted to bind to specific cell types. For example, the modified PE proprotein can be administered as an immunotoxin to further increase its selective toxicity to the desired cells.

The protease is typically expressed within a mammalian cell. The protease within the cell may be native to that cell type, or the cell may be engineered to express a non-native protease. Thus, the present invention has both ex vivo and in vivo utility. Ex vivo utilities include selective elimination of cultured mammalian cells expressing the protease which cleaves the protease activatable sequence. Nucleic acids encoding a PE proprotein can be used as vectors. Disruption of the PE proprotein coding sequence with a nucleic acid insert allows mammalian cells transfected with the vector to survive. Cells transfected with the PE proprotein vector are eliminated. The protease activatable sequence can be modified to be sensitive to the desired protease.

In vivo utilities include increased selective toxicity of PE to particular mammalian cells (e.g., cancer cells) which express proteases which are substantially exclusive to those cells.

In one aspect this invention provides a protease-activatable Pseudomonas exotoxin A-like ("PE-like") proprotein comprising: (1) a cell recognition domain of between 10 and 1500 amino acids that binds to a cell surface-receptor; (2) a modified PE translocation domain comprising an amino acid sequence sufficiently homologous to domain II of PE to effect translocation to a cell cytosol upon proteolytic cleavage, wherein the translocation domain comprises a cysteine-cysteine loop that comprises a protease activatable sequence cleavable by a protease and wherein the cysteine-cysteine loop is substantially un-activatable by furin; (3) optionally, a PE Ib-like domain comprising an amino acid sequence up to 1500 amino acids; (4) a cytotoxicity domain comprising an amino acid sequence substantially homologous to domain III of PE, the cytotoxicity domain having ADP-ribosylating activity; and (5) an endoplasmic reticulum ("ER") retention sequence.

In one embodiment of a PE-like proprotein, the modified PE translocation domain has a PE domain II sequence (amino acids 253–364 of SEQ ID NO:1) modified with amino acids substitutions introducing the protease activatable sequence so as to cause cleavage by the protease between amino acids 279 and 280. In another embodiment the protease activatable sequence is cleavable by a protease secreted by a cancer cell. In another embodiment, the cell recognition domain comprises an antibody that specifically binds to a cancer cell surface marker. In another embodiment, the protease activatable sequence is cleavable by prostate specific antigen ("PSA"), urokinase, neutral endoprotease, stromelysin, collagenase, cathepsin B, or cathepsin D. In another embodiment, the PE Ib-like domain, the cytotoxicity domain and the ER retention. sequence together have the sequence of domains Ib and III of native PE. In other embodiment, the cell recognition domain is coupled to the modified translocation domain through a peptide bond (i.e., as a fusion protein) or through a chemical linkage.

In another aspect, this invention provides a pharmaceutical composition comprising a pharmaceutically acceptable carrier and a therapeutically effective amount of a protease-specific Pseudomonas exotoxin A-like ("PE-like") proprotein of this invention.

In another aspect, this invention provides a recombinant polynucleotide comprising a nucleotide sequence encoding a protease-specific Pseudomonas exotoxin A-like ("PE-like") proprotein of this invention. In one embodiment, the recombinant polynucleotide is an expression vector further comprising an expression control sequence operatively linked to the nucleotide sequence.

In another aspect, this invention provides a method for killing a target cell comprising contacting the cell with a protease-specific Pseudomonas exotoxin A-like ("PE-like") proprotein of this invention. In one embodiment, the cancer cell is, without limitation, a prostate cancer cell, a breast cancer cell or a colon cancer cell.

In another aspect, this invention provides a method for therapeutically treating a subject suffering from cancer comprising administering to the subject a protease-specific Pseudomonas exotoxin A-like ("PE-like") proprotein of this invention. More specifically, the PE-like proprotein comprises a protease activatable sequence that is cleavable by an enzyme produced by the cancer cell. The PE-like proprotein can be administered as a pharmaceutical composition.

BRIEF DESCRIPTION OF THE DRAWINGS

FIGS. 1A–1B. Construction of plasmids for expression of novel immunotoxins containing residues for cleavage and activation by PSA.

A. Plasmids for the expression of the components of the two novel disulfide-stabilized immunotoxins HB21dsFvPE40(sem1) and HB21dsFvPE40(sem2) were constructed through site-directed mutagenesis and multiple cloning steps as described in the Example. Uracil-containing single-stranded DNA from plasmid encoding the single-chain Fv immunotoxin HB21scFvPE38K wa used as a template for site directed mutagenesis (Kunkel T. A., *Proc. Nat'l. Acad. Sci. U.S.A.* 82, pp. 488–492 (1985)). pPWHBVH, encoding HB21VH(cys), was obtained by replacing gly45 with cysteine, introducing a stop codon followed by an EcoRI site at the C-terminus of the anti-transferrin VH gene, and deleting the EcoRI fragment encoding the linker and VL-toxin. To make pPWHB38K, encoding HB21VL(cys)PE38K, we introduced an NdeI site and an ATG translation initiation codon at the N-terminus of the anti-transferrin VL gene, replaced ala238 with cysteine, and subsequently deleted the NdeI fragment encoding the HB21(VH) and linker. Final expression plasmids pPWHB40 (sem1 or 2), encoding HB21VL(cys)PE40(sem1 or 2), were constructed by replacing a BspMI/EcoRI fragment encoding PE38K (domains II and III) from plasmid encoding. HB21VL(cys)PE38K with a BspMI/EcoRI fragment encoding PE40 (domains II, IB, and III) and the inserted semenogelin oligoduplex sequences within domain II from pMOA1A2VK352.

B. Chart showing the relationship between the plasmid constructs, their encoded proteins, the corresponding immunotoxin, and the structure of the immunotoxin and its site of cleavage.

FIG. 2. Sodium dodecyl sulfate-polyacrylamide gel electrophoresis of purified recombinant HB21dsFvPE40(sem) immunotoxins. M, molecular mass standards (sizes in kilodaltons indicated to the left) Non-reduced: lane 1, HB21dsFvPE40(wt); lane 2, HB21dsFvPE40(sem1); lane 3, HB21dsFvPE40(sem2); lane 4 HB21dsFvPE40(sem2W). Reduced: lane 1, HB21dsFvPE40(wt); lane 2, HB21dsFvPE40(sem1); lane 3, HB21dsFvPE40(sem2); lane 4, HB21dsFvPE40(sem2W)

FIG. 3A–3B. Cleavage of recombinant HB21dsFvPE40 (sem) immunotoxins by PSA.

A. Schematic of semenogelin inserts within HB21dsFvPE40. Thirteen to 15 amino acids from domain II of PE were replaced with residues from semenogelin I which are cleaved by PSA. Substrates recognized by furin (WT (SEQ ID NO:23)) or PSA (SEM1 (SEQ ID NO:24) and 2 (SEQ ID NO:25) are underlined.

B. Cleavage of recombinant HB21dsFvPE40(sem) immunotoxins by PSA. Recombinant immunotoxins HB21dsFvPE40(wt), HB21dsFvPE40(sem1), HB21dsFvPE40(sem2), and HB21dsFvPE40(sem2W) were incubated with PSA in 50 mM Tris, 100 mM NaCl (pH 7.0) at a 1:10 molar ratio for 6 hours at 37° C., and cleavage products were analyzed under reducing conditions through SDS-PAGE. Lane M, molecular mass standard (sizes in kilodaltons indicated to the left); lane 1, HB21dsFvPE40 (wt); lane 2, HB21dsFvPE40(sem1); lane 3, HB21dsFvPE40(sem2). The immunotoxin HB21dsFvPE40 (sem2) was cleaved most extensively by PSA (lane 3). PSA-mediated cleavage of all three immunotoxins containing newly engineered PSA sites within domain II yielded 37 kD and 15 kD fragments (lanes 2–3) (confirmed through sequence analysis). Non-specific cleavage of HB21dsFvPE40(wt) resulted in a band slightly larger than 37 kD (lane 1).

FIGS. 4A–4B. Optimizing conditions for PSA-mediated cleavage of HB21dsFvPE40(sem2).

A. PSA-mediated cleavage of HB21dsFvPE40(sem2) at varying enzyme:substrate ratios. HB21dsFvPE40(sem2) was incubated with PSA at various enzyme:substrate ratios (indicated above each lane) in PSA buffer (50 mM Tris, 100 mM NaCl (pH 7.0)) for 6 hrs at 37° C. Cleavage products were analyzed through SDS-PAGE under reducing conditions. Lane M, molecular mass standard (sizes indicated to the left in kilodaltons). Cleavage products generated from specific cleavage within the inserted semenogelin sequence in domain II were 37 kD and 15 kD in size (lanes 3–5). The optimal enzyme:substrate ratio for achieving the greatest amount of specific cleavage and minimizing non-specific cleavage was 1:10 (lane 4).

B. Time course of PSA mediated cleavage of HB21dsFvPE40(sem2). The immunotoxin HB21dsFvPE40 (sem2) was incubated with PSA at a 1:10 molar ratio in PSA buffer at 37° C., and extent of cleavage over time was assayed. Cleavage products were analyzed through SDS-PAGE under reducing conditions. Incubation times are indicated above each lane. Lane M, molecular mass standard (sizes in kilodaltons indicated to the left). Cleavage products generated from specific cleavage within the inserted semenogelin sequence were 37 kD and 15 kD in size (lanes 3–6). An increase in non-specific cleavage products, between 29 and 35 kD in size, appeared over time. The optimal incubation period was at 6 hrs (lane 5).

Figure 5:
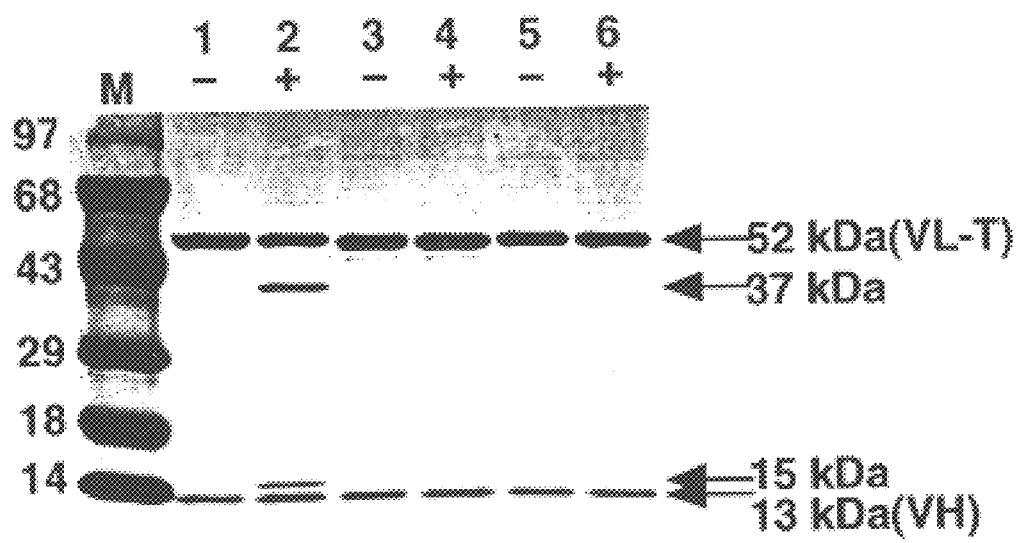

FIG. 5. HB21dsFvPE40(sem) immunotoxins are refractory to cleavage by furin. The three HB21dsFvPE40(sem) immunotoxins and HB21dsFvPE40(wt) were incubated with active furin at a 1:10 molar ratio in furin buffer (0.2 M NaOAc (pH 5.5), 5 mM CaCl2) for 16 hours at 25° C. Cleavage products were analyzed through SDS-PAGE under reducing conditions. Lane M, molecular mass standards (sizes indicated in kilodaltons to the left); lane 1, HB21dsFvPE40(wt)–furin; lane 2, HB21dsFvPE40(wt)+furin; lane 3, HB21dsFvPE40(sem1)–furin; lane 4, HB21dsFvPE40(sem1)+furin; lane 5, HB21dsFvPE40(sem2)–furin; lane 6, HB21dsFvPE40(sem2)+furin. HB21dsFvPE40(wt), which contains an intact furin site, was cleaved to yield the expected 37 kD and 15 kD fragments. The HB21dsFvPE40(sem) immunotoxins, which contain semenogelin I residues in place of the furin cleavage site, were not susceptible to cleavage by furin (lanes 4 and 6).

FIGS. 6A–6B. Cytotoxicity and specificity of HB21dsFvPE40(sem) immunotoxins.

A. Comparison of cytotoxicity of HB21dsFvPE40(wt), HB21dsFvPE40(sem1), and HB21dsFvPE40(sem2) toward DU145 cells which do not express PSA and toward PSA-expressing LNCaP cells in overnight cytotoxicity assays.

B. Comparison of cytotoxicity of HB21dsFvPE40(wt), HB21dsFvPE40(sem1), and HB21dsFvPE40(sem2) pretreated with PSA toward DU145 cells which do not express PSA and toward PSA-expressing LNCaP cells in overnight cytotoxicity assays.

FIG. 7 depicts cleavage of three variants (wtPE, DT8 and DT8ala276=SEQ ID NOs:22, 27 and 28, respectively) by the proteases furin and urokinase (uPA) SEQ ID NOs:26, 27 and 28.

FIG. 8 is a diagram of Pseudomonas Exotoxin A structure. The amino acid position based on SEQ ID NO:2 is indicated. Domain 1a extends from amino acids 1–252. Domain II extends from amino acids 253–364. It includes a cysteine-cysteine loop formed by cysteines at amino acids 265–287. Furin cleaves within the cysteine-cysteine loop between amino acids 279 and 280. A fragment of PE beginning with amino acid 280 translocates to the cytosol. Constructs in which amino acids 345–364 are eliminated also translocate. Domain Ib spans amino acids 365–399. It contains a cysteine-cysteine loop formed by cysteines at amino acids 372 and 379. The domain can be eliminated entirely. Domain III spans amino acids 400–613. Deletion of amino acid 553 eliminates ADP ribosylation activity. The endoplasmic reticulum sequence, REDKL (SEQ ID NO:33) is located at the carboxy-terminus of the molecule, from amino acid 609–613.

FIG. 9 shows the domain II loop of the native PE proprotein (SEQ ID NO:29) including the site of furin-mediated cleavage.

DETAILED DESCRIPTION OF THE INVENTION

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Units, prefixes, and symbols can be denoted in their SI accepted form. Numeric ranges are inclusive of the numbers defining the range. The headings provided herein are not limitations of the various aspects or embodiments of the invention which can be had by reference to the specification as a whole. Accordingly, the terms defined immediately below are more fully defined by reference to the specification in its entirety.

As used herein, “protease activatable sequence” includes reference to an amino acid sequence which is recognized and cleaved by a protease when included within the cysteine-cysteine loop of a modified translocation domain of a PE proprotein. A “non-native protease activatable sequence” includes reference to a protease activatable sequence which is not present in the domain II loop of native PE (e.g., the furin activatable sequence).

As used herein, “activates” includes reference to the formation of a cytotoxic PE-like molecule having an IC50 of no more than 30 ng/ml according to cytotoxicity assays as provided, for example, in the Examples. See also, Brinkmann et al., *Proc. Natl. Acad. Sci. USA,* 88:8616–8620 (1991).

As used herein, “cell specific ligand” includes reference to a binding moiety that preferentially binds to a cell displaying on its surface the binding partner of that binding moiety relative to cells lacking the binding partner. Cell surface receptors are frequently binding partners. Generally, cell specific ligands bind have an affinity for cells displaying the binding partner at least five-fold greater than for cells which lack the binding partner. Examples of such cell specific ligands include, but are not limited to, antibodies, growth factors such as TGFα, IL2, IL4, IL6, IGF1 or CD4, lymphokines, cytokines, hormones and the like which specifically bind desired target cells.

It is, of course, recognized that a certain degree of non-specific interaction may occur between a ligand and a cell surface which substantially lacks the binding partner. Nevertheless, a cell specific ligand may be distinguished as binding through specific recognition of the target molecule. Typically a cell-specific ligand forms a much stronger association to its binding partner than to non-binding partner molecules. For example, antibodies which are cell specific ligands are selected for their specificity for a particular binding partner. The affinity constant of the antibody binding site for its cognate monovalent antigen is at least between $10^6$–$10^7$, usually at least $10^8$ preferably at least $10^9$, more preferably at least $10^{10}$ and most preferably at least $10^{11}$ liters/mole. A variety of immunoassay formats are appropriate for selecting antibodies specifically reactive with a particular protein. For example, solid-phase ELISA immunoassays are routinely used to select monoclonal antibodies specifically reactive with a protein. See Harlow and Lane (1988) Antibodies, A Laboratory Manual, Cold Spring Harbor Publications, New York, for a description of immunoassay formats and conditions that can be used to determine specific reactivity.

As used herein, "mammalian cells" includes reference to cells derived from mammals including but not limited to humans, rats, mice, guinea pigs, chimpanzees, or macaques. The cells may be cultured in vivo or ex vivo.

The term "transfected" includes reference to the introduction of a polynucleotide into a eukaryotic cell where the polynucleotide can be incorporated into the genome of the cell (i.e., chromosome, plasmid, or mitochondrial DNA), converted into an autonomous replicon, or transiently expressed (e.g., transfected mRNA).

The terms "effective amount" or "amount effective to" or "therapeutically effective amount" includes reference to a dosage sufficient to produce a desired result, such as inhibiting cell protein synthesis by at least 20%, 30%, or 40%, or killing the cell.

"Ex vivo" includes reference to introducing a composition into a cell which is outside the body of the organism from which a cell or cells is obtained or from which a cell line is isolated. Ex vivo transfection is often followed by re-infusion of the cells back into the organism.

The terms "immunotoxin conjugate" or "immunotoxin" include reference to a covalent or non-covalent linkage of a toxin to an antibody. The toxin may be linked directly to the antibody, e.g., as a fusion protein, or indirectly through, for example, a linker molecule (e.g., an immune conjugate).

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide nucleic acids ("PNAs"), and the like. Such polynucleotides can be synthesized, for example, using an automated DNA synthesizer. "Nucleic acid" typically refers to large polynucleotides. "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well. Appropriate unicellular hosts include any of those routinely used in expressing eukaryotic or mammalian polynucleotides, including, for example, prokaryotes, such as E. coli; and eukaryotes, including for example, fungi, such as yeast; and mammalian cells, including insect cells (e.g., Sf9) and animal cells such as CHO, R1.1, B-W, L-M, African Green Monkey Kidney cells (e.g. COS 1, COS 7, BSC 1, BSC 40 and BMT 10) and cultured human cells.

"Expression control sequence" refers to a nucleotide sequence in a polynucleotide that regulates the expression (transcription and/or translation) of a nucleotide sequence operatively linked to it. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible, repressible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.*, 82:2306–2309 (1985), or the ciliate Macronucleus, may be used when the nucleic acid is expressed in using the translational machinery of these organisms.

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variant" also refers to polymorphisms in non-coding sequences at a genetic locus and cDNAs derived from mRNA transcripts of genetic allelic variants, as well as the proteins encoded by them.

"Hybridizing specifically to" or "specific hybridization" or "selectively hybridize to," refers to the binding, duplexing, or hybridizing of a polynucleotide preferentially to a particular nucleotide sequence under stringent conditions when that sequence is present in a complex mixture (e.g., total cellular) DNA or RNA.

"Stringent conditions" refers to conditions under which a probe will hybridize preferentially to its target subsequence, and to a lesser extent to, or not at all to, other sequences. "Stringent hybridization" and "stringent hybridization wash conditions" in the context of polynucleotide hybridization experiments such as Southern and northern hybridizations are sequence dependent, and are different under different environmental parameters. An extensive guide to the hybridization of polynucleotides is found in Tijssen (1993) *Laboratory Techniques in Biochemistry and Molecular Biology— Hybridization with Nucleic Acid Probes* part I chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary polynucleotides which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal-to-noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

Conventional notation is used herein to portray polypeptide sequences: the left-hand end of a polypeptide sequence is the amino-terminus; the right-hand end of a polypeptide sequence is the carboxyl-terminus.

Terms used to describe sequence relationships between two or more nucleotide sequences or amino acid sequences include "reference sequence," "selected from," "comparison window," "identical," "percentage of sequence identity," "substantially identical, " "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotide or 4 consecutive amino acid residues that is compared to a reference sequence. The comparison window frequently has a length of at least 15 or at least 25 nucleotides or at least 5 or at least 8 amino acids. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity. Unless otherwise specified, the comparison window used to compare two sequences is the length of the shorter sequence.

When percentage of sequence identity is used in reference to polypeptides it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers & Miller (1988) *Computer Applic. Biol. Sci.* 4:11–17; Smith & Waterman (1981) *Adv. Appl. Math.* 2:482; Needleman & Wunsch (1970) *J. Mol. Biol.* 48:443; Pearson & Lipman (1988) *Proc. Natl. Acad. Sci. USA* 85:2444; Higgins & Sharp (1988) *Gene* 73:237–244; Higgins & Sharp, *CABIOS* 5:151–153 (1989); Corpet et al. (1988) *Nucleic Acids Research* 16:10881–90; Huang et al. (1992) *Computer Applications in the Biosciences* 8:155–65; and Pearson et al. (1994) *Methods in Molecular Biology* 24:307–31. Alignment is also often performed by inspection and manual alignment.

A subject nucleotide sequence or amino acid sequence is "substantially identical" to a reference sequence if the subject amino acid sequence or nucleotide sequence has at least 80% sequence identity over a comparison window. Thus, sequences that have at least 85% sequence identity, at least 90% sequence identity, at least 95% sequence identity, at least 98% sequence identity or at least 99% sequence identity with the reference sequence are also "substantially identical." Two sequences that are identical to each other are, of course, also "substantially identical".

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The amino acids and analogs referred to herein are described by shorthand designations as follows:

| Amino Acid Nomenclature | | |
|---|---|---|
| Name | 3-letter | 1 letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, "antibody" includes reference to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab', F(ab')$_2$, Fab, Fv, rIgG, and, inverted IgG). See, Pierce Catalog and Handbook, 1994–1995 (Pierce Chemical Co., Rockford, Ill.). An antibody immunologically reactive with a particular antigen can be generated in vivo or by recombinant methods such as selection of libraries of recombinant antibodies in phage or similar vectors. See, e.g., Huse et al. (1989) *Science* 246:1275–1281; Ward, et al. (1989) *Nature* 341:544–546; and Vaughan et al. (1996) *Nature Biotechnology*, 14:309–314.

"Substantially pure" means an object species is the predominant species present (i.e., on a molar basis, more abundant than any other individual organic biomolecular species in the composition), and a substantially purified fraction is a composition wherein the object species comprises at least about 50% (on a molar basis) of all organic biomolecular species present. Generally, a substantially pure composition means that about 80% to 90% or more of the organic biomolecular species present in the composition is the purified species of interest. The object species is purified to essential homogeneity (contaminant species cannot be detected in the composition by conventional detection methods) if the composition consists essentially of a single organic biomolecular species. "Organic biomolecule" refers to an organic molecule of biological origin, e.g., proteins, polynucleotides, carbohydrates or lipids. Solvent species, small molecules (<500 Daltons), stabilizers (e.g., BSA), and elemental ion species are not considered organic biomolecular species for purposes of this definition.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Detecting" refers to determining the presence, absence, or amount of an analyte in a sample, and can include quantifying the amount of the analyte in a sample or per cell in a sample.

"Pharmaceutical composition" refers to a composition suitable for pharmaceutical use in a subject. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, or intravenous intraperitoneal injection; or topical, transdermal, or transmucosal administration).

A "subject" of diagnosis or treatment is an animal, such as a mammal, including a human. Non-human animals subject to treatment include, for example, fish, birds, and mammals such as cows, sheep, pigs, horses, dogs and cats.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

"Cysteine-cysteine loop" refers to a peptide moiety in a polypeptide that is defined by an amino acid sequence bordered by two disulfide-bonded cysteine residues.

"Pseudomonas exotoxin A" or "PE" is secreted by *P. aeruginosa* as a 67 kD protein composed of three prominent globular domains (Ia, II, and III) and one small subdomain (Ib) connecting domains II and III. (A. S. Allured et al. (1986) *Proc. Natl. Acad. Sci.* 83:1320–1324.) Domain Ia of PE mediates cell binding. In nature, domain Ia binds to the low density lipoprotein receptor-related protein ("LRP"), also known as the α2-macroglobulin receptor ("α2-MR"). (M. Z. Kounnas et al. (1992) *J. Biol. Chem.* 267:12420–23.) It spans amino acids 1–252. Domain II mediates translocation to the cytosol. It spans amino acids 253–364. Domain Ib has no identified function. It spans amino acids 365–399. Domain III is responsible for cytotoxicity and includes an endoplasmic reticulum retention sequence. It mediates ADP ribosylation of elongation factor 2, which inactivates protein synthesis. It spans amino acids 400–613. PE is "detoxified" if it lacks EF2 ADP ribosylation activity. Deleting amino acid E553 ("ΔE553") from domain III detoxifies the molecule. PE having the mutation ΔE553 is referred to herein as "PE ΔE553." Genetically modified forms of PE are described in, e.g., Pastan et al., U.S. Pat. No. 5,602,095; Pastan et al., U.S. Pat. No. 5,512,658, Pastan et al., U.S. Pat. No. 5,458,878 and Pastan et al., U.S. Pat. No. 5,328,984. Allelic forms of PE are included in this definition. See, e.g., M. L. Vasil et al., (1986) *Infect. Immunol.* 52:538–48. The nucleotide sequence (SEQ ID NO:1) and deduced amino acid sequence (SEQ ID NO:2) of Pseudomonas exotoxin A are:

```
GCC GAA GAA GCT TTC GAC CTC TGG AAC GAA TGC GCC AAA GCC TGC GTG    48
Ala Glu Glu Ala Phe Asp Leu Trp Asn Glu Cys Ala Lys Ala Cys Val
 1               5                  10                  15

CTC GAC CTC AAG GAC GGC GTG CGT TCC AGC CGC ATG AGC GTC GAC CCG    96
Leu Asp Leu Lys Asp Gly Val Arg Ser Ser Arg Met Ser Val Asp Pro
            20                  25                  30

GCC ATC GCC GAC ACC AAC GGC CAG GGC GTG CTG CAC TAC TCC ATG GTC   144
Ala Ile Ala Asp Thr Asn Gly Gln Gly Val Leu His Tyr Ser Met Val
                35                  40                  45

CTG GAG GGC GGC AAC GAC GCG CTC AAG CTG GCC ATC GAC AAC GCC CTC   192
Leu Glu Gly Gly Asn Asp Ala Leu Lys Leu Ala Ile Asp Asn Ala Leu
    50                  55                  60

AGC ATC ACC AGC GAC GGC CTG ACC ATC CGC CTC GAA GGC GGC GTC GAG   240
Ser Ile Thr Ser Asp Gly Leu Thr Ile Arg Leu Glu Gly Gly Val Glu
 65                  70                  75                  80

CCG AAC AAG CCG GTG CGC TAC AGC TAC ACG CGC CAG GCG CGC GGC AGT   288
Pro Asn Lys Pro Val Arg Tyr Ser Tyr Thr Arg Gln Aia Arg Gly Ser
                85                  90                  95

TGG TCG CTG AAC TGG CTG GTA CCG ATC GGC CAC GAG AAG CCC TCG AAC   336
Trp Ser Leu Asn Trp Leu Val Pro Ile Gly His Glu Lys Pro Ser Asn
            100                 105                 110

ATC AAG GTG TTC ATC CAC GAA CTG AAC GCC GGC AAC CAG CTC AGC CAC   384
Ile Lys Val Phe Ile His Glu Leu Asn Ala Gly Asn Gln Leu Ser His
                115                 120                 125

ATG TCG CCG ATC TAC ACC ATC GAG ATG GGC GAC GAG TTG CTG GCG AAG   432
Met Ser Pro Ile Tyr Thr Ile Glu Met Gly Asp Glu Leu Leu Ala Lys
        130                 135                 140
```

```
CTG GCG CGC GAT GCC ACC TTC TTC GTC AGG GCG CAC GAG AGC AAC GAG     480
Leu Ala Arg Asp Ala Thr Phe Phe Val Arg Ala His Glu Ser Asn Glu
145             150                 155                 160

ATG CAG CCG ACG CTC GCC ATC AGC CAT GCC GGG GTC AGC GTG GTC ATG     528
Met Gln Pro Thr Leu Ala Ile Ser His Ala Gly Val Ser Val Val Met
                165                 170                 175

GCC CAG ACC CAG CCG CGC CGG GAA AAG CGC TGG AGC GAA TGG GCC AGC     576
Ala Gln Thr Gln Pro Arg Arg Glu Lys Arg Trp Ser Glu Trp Ala Ser
            180                 165                 190

GGC AAG GTG TTG TGC CTC CTC GAC CCG CTG GAC GGG GTC TAC AAC TAC     624
Gly Lys Val Leu Cys Leu Leu Asp Pro Leu Asp Gly Val Tyr Asn Tyr
                195                 200                 205

CTC GCC CAG CAA CGC TGC AAC CTC GAC GAT ACC TGG GAA GGC AAG ATC     672
Leu Ala Gln Gln Arg Cys Asn Leu Asp Asp Thr Trp Glu Gly Lys Ile
            210                 215                 220

TAC CGG GTG CTC GCC GGC AAC CCG GCG AAG CAT GAC CTG GAC ATC AAA     720
Tyr Arg Val Leu Ala Gly Asn Pro Ala Lys His Asp Leu Asp Ile Lys
225                 230                 235                 240

CCC ACG GTC ATC AGT CAT CGC CTG CAC TTT CCC GAG GGC GGC AGC CTG     768
Pro Thr Val Ile Ser His Arg Leu His Phe Pro Glu Gly Gly Ser Leu
                245                 250                 255

GCC GCG CTG ACC GCG CAC CAG GCT TGC CAC CTG CCG CTG GAG ACT TTC     816
Ala Ala Leu Thr Ala His Gln Ala Cys His Leu Pro Leu Glu Thr Phe
            260                 265                 270

ACC CGT CAT CGC CAG CCG CGC GGC TGG GAA CAA CTG GAG CAG TGC GGC     864
Thr Arg His Arg Gln Pro Arg Gly Trp Glu Gln Leu Glu Gln Cys Gly
        275                 280                 285

TAT CCG GTG CAG CGG CTG GTC GCC CTC TAC CTG GCG GCG CGG CTG TCG     912
Tyr Pro Val Gln Arg Leu Val Ala Leu Tyr Leu Ala Ala Arg Leu Ser
    290                 295                 300

TGG AAC CAG GTC GAC CAG GTG ATC CGC AAC GCC CTG GCC AGC CCC GGC     960
Trp Asn Gln Val Asp Gln Val Ile Arg Asn Ala Leu Aia Ser Pro Gly
305                 310                 315                 320

AGC GGC GGC GAC CTG GGC GAA GCG ATC CGC GAG CAG CCG GAG CAG GCC    1008
Ser Gly Gly Asp Leu Gly Glu Ala Ile Arg Glu Gln Pro Glu Gln Ala
                325                 330                 335

CGT CTG GCC CTG ACC CTG GCC GCC GCC GAG AGC GAG CGC TTC GTC CGG    1056
Arg Leu Ala Leu Thr Leu Ala Ala Ala Glu Ser Glu Arg Phe Val Arg
            340                 345                 350

CAG GGC ACC GGC AAC GAC GAG GCC GGC GCG GCC AAC GCC GAC GTG GTG    1104
Gln Gly Thr Gly Asn Asp Glu Ala Gly Ala Ala Asn Ala Asp Val Val
        355                 360                 365

AGC CTG ACC TGC CCG GTC GCC GCC GGT GAA TGC GCG GGC CCG GCG GAC    1152
Ser Leu Thr Cys Pro Val Ala Ala Gly Glu Cys Ala Gly Pro Ala Asp
370                 375                 380

AGC GGC GAC GCC CTG CTG GAG CGC AAC TAT CCC ACT GGC GCG GAG TTC    1200
Ser Gly Asp Ala Leu Leu Glu Arg Asn Tyr Pro Thr Gly Ala Glu Phe
385                 390                 395                 400

CTC GGC GAC GGC GGC GAC GTC AGC TTC AGC ACC CGC GGC ACG CAG AAC    1248
Leu Gly Asp Gly Gly Asp Val Ser Phe Ser Thr Arg Gly Thr Gln Asn
                405                 410                 415

TGG ACG GTG GAG CGG CTG CTC CAG GCG CAC CGC CAA CTG GAG GAG CGC    1296
Trp Thr Val Glu Arg Leu Leu Gln Ala His Arg Gln Leu Glu Glu Arg
            420                 425                 430

GGC TAT GTG TTC GTC GGC TAC CAC GGC ACC TTC CTC GAA GCG GCG CAA    1344
Gly Tyr Val Phe Val Gly Tyr His Gly Thr Phe Leu Glu Ala Ala Gln
        435                 440                 445

AGC ATC GTC TTC GGC GGG GTG CGC GCG CGC AGC CAG GAC CTC GAC GCG    1392
Ser Ile Val Phe Gly Gly Val Arg Ala Arg Ser Gln Asp Leu Asp Ala
    450                 455                 460
```

-continued

```
ATC TGG CGC GGT TTC TAT ATC GCC GGC GAT CCG GCG CTG GCC TAC GGC    1440
Ile Trp Arg Gly Phe Tyr Ile Ala Gly Asp Pro Ala Leu Ala Tyr Gly
465                 470                 475                 480

TAC GCC CAG GAC CAG GAA CCC GAC GCA CGC GGC CGG ATC CGC AAC GGT    1488
Tyr Ala Gln Asp Gln Glu Pro Asp Ala Arg Gly Arg Ile Arg Asn Gly
                485                 490                 495

GCC CTG CTG CGG GTC TAT GTG CCG CGC TCG AGC CTG CCG GGC TTC TAC    1536
Ala Leu Leu Arg Val Tyr Val Pro Arg Ser Ser Leu Pro Gly Phe Tyr
                500                 505                 510

CGC ACC AGC CTG ACC CTG GCC GCG CCG GAG GCG GCG GGC GAG GTC GAA    1584
Arg Thr Ser Leu Thr Leu Ala Ala Pro Glu Ala Ala Gly Glu Val Glu
                515                 520                 525

CGG CTG ATC GGC CAT CCG CTG CCG CTG CGC CTG GAC GCC ATC ACC GGC    1632
Arg Leu Ile Gly His Pro Leu Pro Leu Arg Leu Asp Ala Ile Thr Gly
        530                 535                 540

CCC GAG GAG GAA GGC GGG CGC CTG GAG ACC ATT CTC GGC TGG CCG CTG    1680
Pro Glu Glu Glu Gly Gly Arg Leu Glu Thr Ile Leu Gly Trp Pro Leu
545                 550                 555                 560

GCC GAG CGC ACC GTG GTG ATT CCC TCG GCG ATC CCC ACC GAC CCG CGC    1728
Ala Glu Arg Thr Val Val Ile Pro Ser Ala Ile Pro Thr Asp Pro Arg
                565                 570                 575

AAC GTC GGC GGC GAC CTC GAC CCG TCC AGC ATC CCC GAC AAG GAA CAG    1776
Asn Val Gly Gly Asp Leu Asp Pro Ser Ser Ile Pro Asp Lys Glu Gln
                580                 585                 590

GCG ATC AGC GCC CTG CCG GAC TAC GCC AGC CAG CCC GGC AAA CCG CCG    1824
Ala Ile Ser Ala Leu Pro Asp Tyr Ala Ser Gln Pro Gly Lys Pro Pro
        595                 600                 605

CGC GAG GAC CTG AAG                                                1639
Arg Glu Asp Leu Lys
        610
```

II. Protease-Activatable Pseudomonas Exotoxin A-Like Proproteins

A. Basic Structure

Protease-activatable Pseudomonas exotoxin A-like ("PE-like") proproteins are polypeptides having structural domains organized, except as provided herein, in the same general sequence as the four structural domains of PE, and having certain functions (e.g., cell recognition, cytosolic translocation, cytotoxicity and endoplasmic reticulum retention) also possessed by the functional domains of P.E. More specifically, the general order is: domain Ia, domain II, domain Ib, domain III. However, as described in more detail herein, domain Ia can be eliminated and replaced by a binding protein chemically coupled to the molecule, or, a cell recognition domain can be inserted just before the ER retention sequence in domain III. Domain Ib can be eliminated. Domain II is positioned to the amino-terminal side of domain III.

In contrast to native PE, the PE-like proproteins of this invention are engineered to eliminate the native furin cleavage site of domain II and to include within domain II of PE (and, preferentially, within a cysteine-cysteine loop of domain II) a protease activatable sequence that is cleavable by a target protease. Preferably, the target protease is a protease produced by a cell targeted for death, e.g., a cancer cell.

Accordingly, PE-like proproteins include the following structural domains comprised of amino acid sequences, the domains imparting particular functions to the proprotein: (1) a "cell recognition domain" that functions as a ligand for a cell surface receptor and that mediates binding of the protein to a cell; (2) a "translocation domain" that mediates translocation from the endosomes to the cytosol and that includes the protease-activatable sequence and is substantially unactivatable by furin; (3) an optional "PE 1b-like domain" of up to 1500 amino acids; (4) a "cytotoxic domain" that functions to kill cells, preferably, by interfering with ADP-ribosylation activity; and (5) an "endoplasmic reticulum ("ER") retention sequence" that functions to translocate the molecule from the endosome to the endoplasmic reticulum, from which it enters the cytosol.

The relationship of PE structure to its function has been extensively studied. The amino acid sequence of PE has been re-engineered to provide new functions, and many amino acids or peptide segments critical and non-critical to PE function have been identified. Accordingly, the PE-like proproteins of this invention can incorporate these structural modifications to PE within the boundaries set forth herein.

B. Cell Recognition Domain

Protease-activatable Pseudomonas exotoxin-like proproteins comprise an amino acid sequence encoding a "cell recognition domain." The cell recognition domain functions as a ligand for a cell surface receptor. It mediates binding of the protein to a cell. Its purpose is to target the proprotein to a cell which will transport the proprotein to the cytosol for processing. The cell recognition domain can be located in the position of domain Ia of PE. However, this domain can be moved out of the normal organizational sequence. More particularly, the cell recognition domain can be inserted upstream of the ER retention sequence. Alternatively the cell recognition domain can be chemically coupled to the toxin. Also, the proprotein can include a first cell recognition domain at the location of the Ia domain and a second cell recognition domain upstream of the ER retention domain.

Such constructs can bind to more than one cell type. See, e.g., R. J. Kreitman et al., *Blood* 90, pp. 252–259 (1992) *Bioconjugate Chem.* 3:63–68.

Because the cell recognition domain functions as a handle to attach the proprotein to a cell, it can have the structure of any polypeptide known to bind to a particular receptor. Accordingly, the domain generally has the size of known polypeptide ligands, e.g., between about 10 amino acids and about 1500 amino acids, or about 100 amino acids and about 300 amino acids.

Several methods are useful for identifying functional cell recognition domains for use in proproteins. One method involves detecting binding between a proprotein that comprises the cell recognition domain with the receptor or with a cell bearing the receptor. Other methods involve detecting entry of the proprotein into the cytosol, indicating that the first step, cell binding, was successful. These methods are described in detail below in the section on testing.

The cell recognition domain can have the structure of any polypeptide that binds to a cell surface receptor. Insofar as it is an object of this invention to target proproteins to cancer cells, in a preferred embodiment, the cell recognition domain specifically binds to a cell surface protein that acts as a maker for a cancer cell. However, in other embodiments, the amino acid sequence is that of domain Ia of PE, thereby targeting the chimeric protein to the $\alpha$2-MR domain. In still further embodiments, domain Ia can be substituted with: growth factors, such as TGF$\alpha$, which binds to epidermal growth factor ("EGF"); IL-2, which binds to the IL-2 receptor; IL-6, which binds to the IL-6 receptor (e.g., activated B cells and liver cells); CD4, which binds to HIV-infected cells); a chemokine (e.g., Rantes, MIP-1$\alpha$ or MIP-1$\beta$), which binds to a chemokine receptor (e.g., CCR5 or fusin (CXCR4)); ligands for leukocyte cell surface receptors, for example, GM-CSF, G-CSF; ligands for the IgA receptor; or antibodies or antibody fragments directed to any receptor (e.g., single chain antibodies against human transferrin receptor). I. Pastan et al. (1992) *Annu. Rev. Biochem.* 61:331–54.

In one embodiment, the cell recognition domain is located in place of domain Ia of PE. In another embodiment, it can be attached to the other moiety of the molecule through a linker. Engineering studies also show that Pseudomonas exotoxin can be targeted to certain cell types by introducing a cell recognition domain upstream of the ER retention sequence, which is located at the carboxy-terminus of the polypeptide. For example, TGF$\alpha$ has been inserted into domain III just before amino acid 604, i.e., about ten amino acids from the carboxy-terminus. This chimeric protein binds to cells bearing EGF receptor. Pastan et al., U.S. Pat. No. 5,602,095.

In preferred embodiments, the PE-like proproteins of the present invention can be modified with a cell specific ligand to target the PE-like proproteins to particular cells. PE-like proproteins so modified preferentially bind to cells displaying the binding partner to that ligand. In a preferred embodiment, the cell specific ligand is an antibody; thereby, the proprotein is an immunotoxin. Cell specific ligands which are proteins can often be formed in part or in whole as a fusion protein with the PE-like proproteins of the present invention. A "fusion protein" includes reference to a polypeptide formed by the joining of two or more polypeptides through a peptide bond formed by the amino terminus of one polypeptide and the carboxyl terminus of the other polypeptide. The fusion protein may be formed by the chemical coupling of the constituent polypeptides but is typically expressed as a single polypeptide from a nucleic acid sequence encoding the single contiguous fusion protein. Included among such fusion proteins are single chain Fv fragments (scFv). Particularly preferred targeted PE-like proproteins are disulfide stabilized immunotoxins which can be formed in part as a fusion protein as exemplified herein. Other protein cell specific ligands can be formed as fusion proteins using cloning methodologies well known to the skilled artisan.

Attachment of cell specific ligands also can be accomplished through the use of linkers. A "linker," as used herein, is a molecule that is used to join two molecules. The linker is capable of forming covalent bonds or high-affinity non-covalent bonds to both molecules. Suitable linkers are well known to those of ordinary skill in the art and include, but are not limited to, straight or branched-chain carbon linkers, heterocyclic carbon linkers, or peptide linkers. The linkers may be joined to the constituent amino acids through their side groups (e.g., through a disulfide linkage to cysteine).

In one embodiment, protease-activatable PE-like proproteins are immunotoxins directed against particular cancer cells. Accordingly, the cell recognition domain is an antibody that specifically binds to a cell surface receptor or marker specific for a cancer cell. This includes, for example, prostate cancer cells, breast cancer cells or colon cancer cells. In alternative embodiments, the proprotein can be a fusion protein or a conjugate protein. In the fusion protein, domain Ia is replaced with a polypeptide sequence for an immunoglobulin heavy chain from an immunoglobulin specific for the cancer cell. The light chain of the immunoglobulin can be co-expressed with the proprotein so as to form a light chain-heavy chain dimer. In the conjugate protein, the antibody is chemically linked to a polypeptide comprising the other domains of the proprotein.

The procedure for attaching a PE-like proprotein to an antibody or other cell specific ligand will vary according to the chemical structure of the toxin. Antibodies contain a variety of functional groups; e.g., sulfhydryl (—S), carboxylic acid (COOH) or free amine ($—NH_2$) groups, which are available for reaction with a suitable functional group on a toxin. Additionally, or alternatively, the antibody or PE-like proprotein can be derivatized to expose or attach additional reactive functional groups. The derivatization may involve attachment of any of a number of linker molecules such as those available from Pierce Chemical Company, Rockford Ill.

A bifunctional linker having one functional group reactive with a group on the PE-like proprotein, and another group reactive with a cell specific ligand, can be used to form a desired conjugate. Alternatively, derivatization may involve chemical treatment of the PE-like proprotein or the cell specific ligand, e.g., glycol cleavage of the sugar moiety of a glycoprotein antibody with periodate to generate free aldehyde groups. The free aldehyde groups on the antibody may be reacted with free amine or hydrazine groups on the antibody to bind the PE-like proprotein thereto. (See U.S. Pat. No. 4,671,958). Procedures for generation of free sulfhydryl groups on antibodies or other proteins, are also known (See U.S. Pat. No. 4,659,839).

Many procedures and linker molecules for attachment of various compounds including toxins are known. See, for example, European Patent Application No. 188,256; U.S. Pat. Nos. 4,671,958, 4,659,839, 4,414,148, 4,699,784; 4,680,338; 4,569,789; 4,589,071; and Borlinghaus et al. *Cancer Res.* 47: 4071–4075 (1987). In particular, production of various immunotoxin conjugates is well-known within the art and can be found, for example in "Monoclonal Antibody-Toxin Conjugates: Aiming the Magic Bullet,"

Thorpe et al., *Monoclonal Antibodies in Clinical Medicine*, Academic Press, pp. 168–190 (1982), Waldmann, *Science*, 252: 1657 (1991), U.S. Pat. Nos. 4,545,985 and 4,894,443 which are incorporated herein by reference. See also, e.g., Birch and Lennox, *Monoclonal Antibodies: Principles and Applications*, Chapter 4, Wiley-Liss, New York, N.Y. (1995); U.S. Pat Nos. 5,218,112, 5,090,914; Hermanson, *Bioconjugate Techniques*, Academic Press, San Diego, Calif. (1996).

In some circumstances, it is desirable to free the PE-like proprotein from the antibody or other cell specific ligand when the conjugate has reached its target site. Therefore, conjugates comprising linkages which are cleavable in the vicinity or within the target site may be used when the toxin is to be released at the target site. Cleaving of the linkage to release the agent from the ligand may be prompted by enzymatic activity or conditions to which the immunoconjugate is subjected either inside the target cell or in the vicinity of the target site. A number of different cleavable linkers are known to those of skill in the art. See U.S. Pat. Nos. 4,618,492; 4,542,225, and 4,625,014. SPDP is a reversible NHS-ester, pyridyl disulfide cross-linker used to conjugate amine-containing molecules to sulfhydryls. Another chemical modification reagent is 2-iminothiolane which reacts with amines and yields a sulfhydryl. Water soluble SPDP analogs, such as Sulfo-LC-SPDP (Pierce, Rockford, Ill.) are also available. SMPT is a reversible NHS-ester, pyridyl disulfide cross-linker developed to avoid cleavage in vivo prior to reaching the antigenic target. Additionally, the NHS-ester of SMPT is relatively stable in aqueous solutions.

C. PE-Like Translocation Domain

Protease-activatable PE-like proproteins also comprise an amino acid sequence encoding a "modified PE translocation domain." The modified PE translocation domain includes a cysteine-cysteine loop that includes a protease activatable sequence, and is engineered to eliminate the native furin recognition site. It comprises an amino acid sequence sufficient to effect translocation of chimeric proteins that have been endocytosed by the cell into the cytosol. A proprotein that does not contain the sequence RXXR (SEQ ID NO:30) with in the cysteine-cysteine loop is substantially un-activatable by furin and, consequently, substantially non-toxic to cells not having an enzyme that cleaves the protease-activatable sequence. The amino acid sequence generally is substantially identical to a sequence selected from domain II of PE. Upon cleavage by a protease that recognizes the protease-activatable sequence and reduction of the disulfide bond, the proprotein is now activated, i.e., is enabled for translocation into the cytosol and subsequent cytotoxic activity.

More specifically, protease-activatable PE-like proproteins comprise a cysteine-cysteine loop that comprises the protease activatable sequence. The loop generally has between about 10 and 50 amino acids, more preferably, about 23 amino acids, as in native PE. The protease activatable sequence can be located anywhere within the cysteine-cysteine loop. Preferably, the sequence is more than 5 amino acids from the cysteine residues involved in the disulfide bond. More preferably, the cysteine-cysteine loop has the sequence of the loop in native PE except for substitutions that introduce the protease activatable sequence. The cysteine-cysteine loop also is modified to eliminate the native furin recognition sequence. Furin recognizes the sequence RXXR (SEQ ID NO:30), wherein X is any amino acid. This sequence occurs in native PE at amino acids 276–279.

According to nomenclature developed to define the area around the cleavage site, "P" numbers designate amino acids toward the amino-terminus of the molecule, while "P'" numbers identify the cleavage site toward the carboxy-terminus. Thus, in native PE, the cleavage site has the sequence RQPR/GWEQ (SEQ ID NO:31), wherein the slash indicates the cleavage site. These amino acids are designated P4, P3, P2, P1/P'1, P'2, P'3 and P'4, respectively. Accordingly, in a preferred embodiment, the protease-activatable sequence is positioned so that P1 and P'1 are located at positions 279 and 280 of PE, when the sequence of proprotein is optimally aligned with native PE.

The amino acid sequence sufficient to effect translocation can derive from the translocation domain of native PE. This domain spans amino acids 253–364. The translocation domain can include the entire sequence of domain II. However, the entire sequence is not necessary for translocation. For example, the amino acid sequence can minimally contain, e.g., amino acids 280–344 of domain II of PE. Sequences outside this region, i.e., amino acids 345–364, can be eliminated from the domain. Amino acids 253–264 also can be eliminated or substituted, however, the construct should contain a cysteine-cysteine loop. This domain also can be engineered with substitutions, preferably conservative, so long as translocation activity is retained.

The translocation domain functions as follows. After binding to a receptor on the cell surface, the chimeric proteins enter the cell by endocytosis through clathrin-coated pits. Residues 265 and 287 are cysteines that form a disulfide loop. Once internalized into endosomes having an acidic environment, the peptide is cleaved by the protease furin between Arg279 and Gly280. Then, the disulfide bond is reduced. A mutation at Arg279 inhibits proteolytic cleavage by furin and subsequent translocation to the cytosol. M. Ogata et al. (1990) *J. Biol. Chem.* 265:20678–85. However, a fragment of PE containing the sequence downstream of Arg279 (called "PE37") retains substantial ability to translocate to the cytosol. C. B. Siegall et al. (1989) *J. Biol. Chem.* 264:14256–61. Sequences in domain II beyond amino acid 345 also can be deleted without inhibiting translocation. Furthermore, amino acids at positions 339 and 343 appear to be necessary for translocation. C. B. Siegall et al. (1991) *Biochemistry* 30:7154–59.

Methods for determining the functionality of a translocation domain are described below in the section on testing.

Preferably, the translocation domain comprises a protease activatable sequence containing as few amino acids as required for recognition and cleavage by the cognate protease so that disruption of the native cysteine-cysteine loop sequence is minimized. Further, the cysteine-cysteine loop will typically lack cysteine residues which may compete with the cysteine residues at positions 265 and 287 for disulfide bonding. The protease activatable sequence will be a non-native (i.e., non-wildtype) cysteine-cysteine loop sequence.

Amino acid sequences that can serve as protease activatable sequences are chosen from peptide substrates of the desired protease. Proteases and their amino acid sequence substrates are well known in the art. For example, urokinase is an enzyme found in many metastatically active cancers. The sequence of urokinase is described by Nagai et al., *Gene,* 36:183–188 (1985); Riccio et al. *Nucl. Acids Res.,* 13:2759–2771 (1985); and, Holmes et al., *Bio/Technology* 3:923–929 (1985), all of which are incorporated herein by reference. Peptide substrates for urokinase ("urokinase activatable sequences) include the sequences: DR/VYIHPF (SEQ ID NO:3) from angiotensin, VVCGER JGFFYTP (SEQ ID NO:4) from the insulin B chain, FFYTPK/A (SEQ ID NO:5), and from adrenal corticotrophic hormone (ACTH) the sequences: KRRPVK/VYP (SEQ ID NO:6), PVGKKR/RPVKVY (SEQ ID NO:7), KPVGKK/RRPVKV (SEQ ID NO:8), and GKPVGK/KRRPVK (SEQ ID NO:9), where "/" indicates the cleavage site. In particularly preferred embodiments, the urokinase activatable sequence has the sequence TFAGNAVRRISVGQ (SEQ ID NO:10). Generally, SEQ ID NO:10 is inserted between residues 271 and 283 of the PE-like proprotein. The sequences of the urokinase activatable sequences disclosed above can be shortened by one or two amino acid residues at the carboxyl and/or amino terminal ends such that at least two residues of the prototype sequences are maintained on either side of the cleavage site.

In other embodiments, the protease activatable sequence is derived from any substrate of prostate-specific antigen ("PSA"). This includes, for example, semenogelin I or semenogelin II, or insulin-like growth factor binding protein. A preferred protease activatable sequence is derived from semenogelin I. Protease activatable sequences from semenogelin I (PSA activatable sequences) include: sem 1 having the sequence SKGSFSIQY/TYHV (SEQ ID NO:11), sem 3 having the sequence HLGGSQQLL/HNKQ (SEQ ID NO:12), and sem 5 having the sequence SKGKGTSSQY/SNTE (SEQ ID NO:13), where "/" indicates the cleavage at position 279. In particularly preferred embodiments the sem 1, sem 3, and sem 5 protease activatable sequences are substituted for the native PE-like proprotein amino acids residing between residues 271 and 283. The sequences of the PSA activatable sequences disclosed above can be shortened by one or two amino acid residues at the carboxyl and/or amino terminal ends such that at least two residues of the prototype sequences are maintained on either side of the cleavage site.

In other embodiments the protease activatable sequence is cleaved by Factor Xa (Nagai and Thogersen, Nature, 309:810–812 (1984); Aurell et al., *Thrombosis Res.,* 11:595–609 (1984)). Factor Xa is readily available from commercial sources such as Pierce Chemical Co. (Rockford, Ill.). Factor Xa cleaves the last amino acid in the sequence Ile-Glu-Gly-Arg (SEQ ID NO:32). Thus, in the present invention the aforementioned factor Xa activatable sequence should extend to amino acid residues 278 or 279.

In additional embodiments the protease activatable sequence will be recognized and cleaved by neutral endoprotease (EC 3.4.24.11, "NEP"). See, Erdos et al., *J. Biol. Chem.,* 264 (24):14519–14523 (1989). NEP is identical with the common acute lymphoblastic leukemia antigen (CALLA). Neutral endoprotease cleaves at the amino side of hydrophobic amino acids. For example, neutral endoprotease cleaves enkephalins at Gly-Phe into a tripeptide and a dipeptide. Other substrates for neutral endoprotease include bradykinin, and the atrial natriuretic peptide. Accordingly, these substrates can be employed as protease activatable sequences with the cognate protease neutral endoprotease (i.e., as "neutral endoprotease activatable sequences").

Other proteases which can be employed in the present invention include, but are not limited to, stromelysin, collagenase, cathepsin B, and cathepsin D.

D. PE 1b-like Domain

Protease activatable PE-like proproteins optionally include an amino acid sequence encoding a "PE lb-like domain." The PE 1b-like domain is located at the native lb domain location of PE, between the translocation domain (e.g., domain II) and the cytotoxic domain (e.g., domain III). The PE 1b-like domain can be up to about 1500 amino acids. This includes domains having between about 15 amino acids and about 350 amino acids or about 15 amino acids and about 50 amino acids.

In native Pseudomonas exotoxin A, domain Ib spans amino acids 365 to 399. The native Ib domain is structurally characterized by a disulfide bond between two cysteines at positions 372 and 379. Domain Ib is not essential for cell binding, translocation, ER retention or ADP ribosylation activity. Therefore, it can be entirely re-engineered or eliminated completely. The PE 1b-like domain can be linear or it can include a cysteine-cysteine loop.

E. Cytotoxicity Domain and ER Retention Sequence

PE-like proproteins also comprise an amino acid sequence encoding a "cytotoxicity domain" and an "endoplasmic reticulum ('ER') retention sequence." The cytotoxicity domain has a sequence sufficiently complementary to domain III of native PE to confer ADP-ribosylating activity, thereby rendering the construct cytotoxic. The ER retention sequence functions in translocating the proprotein to from the endosome to the endoplasmic reticulum, from where it is transported to the cytosol. The cytotoxic domain is located at the position of domain III in PE.

The cytotoxic domain comprises an amino acid sequence that has, at its carboxy terminus, an ER retention sequence. The ER retention sequence in native PE is REDLK (SEQ ID NO:38). Lysine can be eliminated (i.e., REDL) without a decrease in activity. REDLK (SEQ ID NO:33) can be replaced with other ER retention sequences, such as KDEL (SEQ ID NO:35), or polymers of these sequences. M. Ogata et al. (1990) *J. Biol. Chem.* 265:20678–85. Pastan et al., U.S. Pat. No. 5,458,878. I. Pastan et al. (1992) *Annu. Rev. Biochem.* 61:331–54.

In native PE, domain III has two functions. It exhibits ADP-ribosylating activity and directs endocytosed toxin into the endoplasmic reticulum. The ribosylating activity of PE is located between about amino acids 400 and 600 of PE. ADP ribosylation activity is eliminated by, for example, deleting amino acid E553 ("ΔE553"). M. Lukac et al. (1988) *Infect. and Immun.* 56:3095–3098.

Activity of this domain can be assessed by testing for translocation of the protein into the target cell cytosol using the assays described below.

In one embodiment, the sequence of the cytotoxic domain and ER retention sequence is substantially identical to the native amino acid sequences of the domain III, or a fragment of it including, e.g., conservative substitutions that do not alter function. In one embodiment, the cytotoxic domain and ER retention sequence is domain III of PE.

In another embodiment, a cell recognition domain is inserted into the amino acid sequence ahead of the ER retention sequence (e.g., into domain III). For example, the cell recognition domain can be inserted just up-stream of the ER retention sequence, so that the ER retention sequence is connected directly or within ten amino acids of the carboxy terminus of the cell recognition domain.

F. Methods of Making PE-like Proproteins

PE-like proproteins preferably are produced recombinantly, as described below. This invention also envisions the production of PE chimeric proteins by chemical synthesis using methods available to the art.

G. Testing PE-like Proproteins

Having selected various structures as domains of the proprotein, the function of these domains, and of the proprotein as a whole, can be tested to detect functionality. PE-like proproteins can be tested for cell recognition, cleavability, cytosolic translocation and cytotoxicity using routine assays. The entire proprotein protein can be tested, or, the function of various domains can be tested by substituting them for native domains of the wild-type toxin.

1. Receptor binding/Cell recognition The function of the cell binding domain can be tested as a function of the proprotein to bind to the target receptor either isolated or on the cell surface.

In one method, binding of the proprotein to a target is performed by affinity chromatography. For example, the proprotein can be attached to a matrix in an affinity column, and binding of the receptor to the matrix detected.

Binding of the proprotein to receptors on cells can be tested by, for example, labeling the proprotein and detecting its binding to cells by, e.g., fluorescent cell sorting, autoradiography, etc.

If antibodies have been identified that bind to the ligand from which the cell recognition domain is derived, they also are useful to detect the existence of the cell recognition domain in the chimeric immunogen by immunoassay, or by competition assay for the cognate receptor.

2. Protease-activatable cleavage

The function of the protease-activatable sequence can be tested by cleavage assays in which the proprotein is exposed to the protease that recognizes it. The production of the polypeptide fragments resulting from cleavage is detected. Such assays are described in more detail in the Examples.

3. Translocation to the cytosol

The function of the translocation domain and the ER retention sequence can be tested as a function of the proprotein's ability to gain access to the cytosol. Because access first requires binding to the cell, these assays also are useful to determine whether the cell recognition domain is functioning.

a. Presence in the Cytosol

In one method, access to the cytosol is determined by detecting the physical presence of the proprotein in the cytosol. For example, the proprotein can be labelled and the proprotein exposed to the cell. Then, the cytosolic fraction is isolated and the amount of label in the fraction determined. Detecting label in the fraction indicates that the proprotein has gained access to the cytosol.

4. Cytotoxicity (ADP Ribosylation activity)

In another method, the ability of the translocation domain and ER retention sequence to effect translocation to the cytosol can be tested with a construct containing a domain III having ADP ribosylation activity. Briefly, cells are seeded in tissue culture plates and exposed to the PE-like proprotein or to an engineered PE exotoxin containing the modified translocation domain or ER retention sequence in place of the native domains. ADP ribosylation activity is determined as a function of inhibition of protein synthesis by, e.g., monitoring the incorporation of $^3$H-leucine.

III. Recombinant Polynucleotides Encoding PE-Like Proproteins

A. Recombinant Polynucleotides

1. Sources

With the protease activatable sequences herein provided, and the PE sequence as disclosed in SEQ ID NO:1, one of skill can readily construct a variety of clones containing functionally equivalent nucleic acids, such as nucleic acids which differ in sequence but which encode the same PE-like proprotein. PE-like proprotein related compositions such as PE-like proprotein fusion proteins comprising a cell-specific ligand can also be constructed. Cloning methodologies to accomplish these ends, and sequencing methods to verify the sequence of nucleic acids are well known in the art and exemplified herein. Other examples of appropriate cloning and sequencing techniques, and instructions sufficient to direct persons of skill through many cloning exercises are found in Sambrook, et al., *Molecular Cloning: A Laboratory Manual* (2nd Ed., Vols. 1–3, Cold Spring Harbor Laboratory (1989)), *Methods in Enzymology,* Vol. 152: *Guide to Molecular Cloning Techniques* (Berger and Kimmel (eds.), San Diego: Academic Press, Inc. (1987)), or *Current Protocols in Molecular Biology,* (Ausubel, et al. (eds.), Greene Publishing and Wiley-Interscience, New York (1987).

Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Polynucleotides encoding PE-like proproteins or subsequences thereof, such as a protease activatable sequence, can be prepared by any suitable method including, for example, cloning and restriction of appropriate sequences as discussed supra, or by direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); the solid phase phosphoramidite triester method described by Beaucage and Caruthers (1981), *Tetrahedron Letts.,* 22(20): 1859–1862, e.g., using an automated synthesizer, e.g., as described in Needham-VanDevanter et al. (1984) *Nucleic Acids Res.,* 12:6159–6168; and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Nucleic acids encoding native PE exotoxin can be modified to form the PE-like proproteins of -the present invention. Modification by site-directed mutagenesis is well known in the art. Native PE exotoxin nucleic acids can be amplified by in vitro methods. Amplification methods include the polymerase chain reaction (PCR), the ligase chain reaction (LCR), the transcription-based amplification system (TAS), the self-sustained sequence replication system (SSR). A wide variety of cloning methods, host cells, and in vitro amplification methodologies are well-known to persons of skill.

Mutant versions of the proteins can be made by site-specific mutagenesis of other polynucleotides encoding the proteins, or by random mutagenesis caused by increasing the error rate of PCR of the original polynucleotide with 0.1 mM $MnCl_2$ and unbalanced nucleotide concentrations.

Once the nucleic acids encoding an PE-like proprotein of the present invention is isolated and cloned, one may express the desired protein in a recombinantly engineered cell such as bacteria, yeast, insect and mammalian cells. It is expected that those of skill in the art are knowledgeable in the numerous expression systems available for expression of proteins. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to an expression control sequence (e.g., a promoter which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the protein. To obtain high level expression of a cloned gene, it is desirable to construct expression vectors which contain, at the minimum, a strong promoter to direct transcription, a ribosome binding site for translational initiation, and a transcription/translation terminator.

One of skill would recognize that modifications can be made to a nucleic acid encoding a PE-like proprotein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A variety of means are available for delivering polynucleotides to cells including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. See also Inouye et al., U.S. Pat. No. 5,272,065; *Methods in Enzymology,* vol. 185, Academic Press, Inc., San Diego, Calif. (D. V. Goeddel, ed.) (1990) or M. Krieger, *Gene Tran ser and Expression—A Laboratory Manual,* Stockton Press, New York, N.Y., (1990). Recombinant DNA expression plasmids can also be used to prepare the polynucleotides of the invention for delivery by means other than by gene therapy, although it may be more economical to make short oligonucleotides by in vitro chemical synthesis.

The construct can also contain a tag to simplify isolation of the protein. For example, a polyhistidine tag of, e.g., six histidine residues, can be incorporated at the amino terminal end of the protein. The polyhistidine tag allows convenient isolation of the protein in a single step by nickel-chelate chromatography.

Nucleic acids encoding PE-like proproteins of the present invention may be expressed in a variety of host cells, including *E. coli,* other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences. The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, the PE-like proproteins of the present invention may then be used therapeutically.

The PE-like proproteins of the present invention can also be constructed in whole or in part using standard synthetic methods. Solid phase synthesis of isolated proteins of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, *Solid-Phase Peptide Synthesis;* pp. 3–284 in *The Peptides: Analysis, Synthesis, Biology.* Vol. 2: *Special Methods in Peptide Synthesis,* Part A., Merrifield, et al. *J. Am. Chem. Soc.,* 85: 2149–2156 (1963), and *Stewart et al., Solid Phase Peptide Synthesis,* 2nd ed. Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N, N'-dicycylohexylcarbodiimide)) is known to those of skill.

Eliminating nucleotides encoding amino acids 1–252 yields a construct referred to as "PE40." Eliminating nucleotides encoding amino acids 1–279 yields a construct referred to as "PE37." (See Pastan et al., U.S. Pat. No. 5,602,095.) The practitioner can ligate sequences encoding cell recognition domains to the 5'end of these platforms to engineer PE-like chimeric proteins that are directed to particular cell surface receptors. These constructs optionally can encode an amino-terminal methionine. A cell recognition domain can be inserted into such constructs in the nucleotide sequence encoding the ER retention sequence.

The construct also can be engineered to encode a secretory sequence at the amino terminus of the protein. Such constructs are useful for producing the proteins in mammalian cells.

IV. Antibody Production

In preferred embodiment, the PE-like proproteins of the present invention are attached to antibodies to form immunotoxins. Particularly preferred are disulfide stabilized antibodies as exemplified herein. The attachment may be by covalent or non-covalent means (e.g., biotin and avidin). Typically, covalent attachment can be accomplished by construction of fusion proteins or by the use of chemical linkers as discussed, supra. The following discussion is presented as a general overview of the techniques available; however, one of skill will recognize that many variations upon the following methods are known.

A. Antibody Production

Methods of producing polyclonal antibodies are known to those of skill in the art. In brief, an immunogen (antigen) is mixed with an adjuvant and animals are immunized with the mixture. The immunogen is preferably a purified cell surface antigen which forms the binding partner for the antibody. Alternatively, the cell surface antigen is coupled to an appropriate carrier (e.g., GST, keyhole limpet hemocyanin, or equivalents), or a nucleic acid encoding the cell surface antigen is incorporated into an immunization vector such as a recombinant vaccinia virus (see, U.S. Pat. No. 4,722,848) The animal's immune response to the immunogen preparation is monitored by taking test bleeds and determining the titer of reactivity to the cell surface antigen of interest. When appropriately high titers of antibody to the immunogen are obtained, blood is collected from the animal and antisera are prepared. Further fractionation of the antisera to enrich for antibodies reactive to the cell surface antigen is performed where desired (see, e.g., Coligan (1991) *Current Protocols in Immunology* Wiley/Greene, N.Y.; and Harlow and Lane (1989) *Antibodies: A Laboratory Manual* Cold Spring Harbor Press, NY).

Antibodies, including binding fragments and single chain recombinant versions thereof, against predetermined fragments of the desired cell surface antigen are raised by immunizing animals, e.g., with conjugates of the fragments with carrier proteins as described above. Typically, the immunogen of interest is a cell surface antigen of at least about 5 amino acids in length, more typically the cell surface antigen is at least 10 amino acids in length, preferably, at least 15 amino acids in length, more preferably at least 25 amino acids in length. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a cell surface antigen from which the immunogen was derived. Specific monoclonal and polyclonal antibodies will usually bind with an affinity constant of at least $10^{-6}$-$10^{-7}$ M, preferably at least $10^{-8}$ M, preferably at least $10^{-9}$ M, more preferably at least $10^{-10}$ M, most preferably at least $10^{-11}$ M.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method proceeds by injecting an animal with an immunogen comprising a cell surface antigen. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transfection with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host.

Other suitable techniques involve selection of libraries of recombinant antibodies in phage or similar vectors (see, e.g., Huse et al. (1989) *Science* 246: 1275–1281; and Ward, et al. (1989) *Nature* 341: 544–546; and Vaughan et al. (1996) *Nature Biotechnology*, 14: 309–314). Alternatively, high avidity human monoclonal antibodies can be obtained from transgenic mice comprising fragments of the un-rearranged human heavy and light chain Ig loci (i.e., minilocus transgenic mice). Fishwild et al., *Nature Biotech.*, 14:845–851 (1996).

B. Human or Humanized (Chimeric) Antibody Production

Antibodies administered to an organism other than the species in which they are raised are often immunogenic. Thus, for example, murine antibodies administered to a human often induce an immunologic response against the antibody (e.g., the human anti-mouse antibody (HAMA) response) on multiple administrations. The immunogenic properties of the antibody are reduced by altering portions, or all, of the antibody into characteristically human sequences thereby producing chimeric or human antibodies, respectively.

1. Humanized (Chimeric) Antibodies

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Patent Nos: U.S. Pat. No. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

2. Human Antibodies

In another embodiment, this invention provides for fully human antibodies which serve as cell specific ligands for construction of PE-like proproteins. Human antibodies consist entirely of characteristically human polypeptide sequences. The human antibodies of this invention can be produced in using a wide variety of methods (see, e.g., Larrick et al., U.S. Pat. No. 5,001,065, for review).

In some embodiments, the human antibodies of the present invention are usually produced initially in trioma cells. Genes encoding the antibodies are then cloned and expressed in other cells, particularly, nonhuman mammalian cells. The general approach for producing human antibodies by trioma technology has been described by Ostberg et al. (1983), *Hybridoma* 2: 361–367, Ostberg, U.S. Pat. No. 4,634,664, and Engelman et al., U.S. Pat. No. 4,634,666. The antibody-producing cell lines obtained by this method are called triomas because they are descended from three cells; two human and one mouse. Triomas have been found to produce antibody more stably than ordinary hybridomas made from human cells.

The genes encoding the heavy and light chains of immunoglobulins secreted by trioma cell lines are cloned according to methods, including the polymerase chain reaction, known in the art (see, e.g., Sambrook et al., *Molecular Cloning: A Laboratory Manual*, 2nd ed., Cold Spring Harbor, N.Y., 1989; Berger & Kimmel, *Methods in*

*Enzymology,* Vol. 152: *Guide to Molecular Cloning Techniques,* Academic Press, Inc., San Diego, Calif., 1987; Co et al. (1992) *J. Immunol.,* 148: 1149). For example, genes encoding heavy and light chains are cloned from a trioma's genomic DNA or CDNA produced by reverse transcription of the trioma's RNA. Cloning is accomplished by conventional techniques including the use of PCR primers that hybridize to the sequences flanking or overlapping the genes, or segments of genes, to be cloned.

V. Transfection of Mammalian Cells

The present invention provides nucleic acids encoding proteases for cleavage of the desired protease activatable sequence (protease nucleic acids). The mammalian cells can be altered to express the cognate protease to a particular protease activatable sequence. Thus, mammalian cells can be altered for susceptibility to a particular PE-like proprotein.

The present invention also provides nucleic acids encoding the PE-like proprotein compositions of the present invention (PE-like proprotein nucleic acids). These PE-like proproteins can be used to inhibit protein synthesis in recombinant or native cells expressing the cognate protease.

Nucleic acids of the present invention include those for transfection of mammalian cells ex vivo and in vivo. These nucleic acids can be inserted into any of a number of well known vectors for the transfection of target cells and organisms as described below. The nucleic acids are transfected into cells, ex vivo or in vivo, through the interaction of the vector and the target cell. Nucleic acids of the present invention are discussed more fully, supra.

For a review of gene therapy procedures, see Anderson, *Science* (1992) 256:808–813; Nabel and Felgner (1993) *TIBTECH* 11: 211–217; Mitani and Caskey (1993) *TIBTECH* 11: 162–166; Mulligan (1993) *Science* 926–932; Dillon (1993) *TIBTECH* 11: 167–175; Miller (1992) *Nature* 357: 455460; Van Brunt (1988) *Biotechnology* 6(10): 1149–1154; Vigne (1995) *Restorative Neurology and Neuroscience* 8: 35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Therapy* (1994) 1:13–26. Ex vivo transfection of mammalian cells which are not intended for use in therapeutic gene therapy applications (e.g., for re-infusion) can be achevied using standard molecular biology methods as described, supra.

Delivery of the target nucleic acid into the mammalian cell is the first critical step in gene therapy treatment of disease. A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414), and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4:43, and Cornetta et al. *Hum. Gene Ther.* 2:215 (1991)). Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra).

AAV-based vectors are also used to transfect mammalian cells with target nucleic acids, e.g., in the in vitro production of nucleic acids and peptides, and in vivo and ex vivo gene therapy procedures. See, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin.* Invst. 94:1351 and Samulski (supra) for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11):3251–3260; Tratschin, et al. (1984) *Mol. Cell. Biol.,* 4:2072–2081; Hermonat and Muzyczka (1984) *Proc. Natl. Acad. Sci. USA,* 81:6466–6470; McLaughlin et al. (1988) and Samulski et al. (1989) *J. Virol.,* 63:03822–3828. Cell lines that can be transfected by rAAV include those described in Lebkowski et al. (1988) *Mol. Cell. Biol.,* 8:3988–3996.

A. Ex vivo Transfection of Cells

Ex vivo mammalian cell transfection for gene therapy (e.g., via re-infusion of the transfected cells into the host organism) is well known to those of skill in the art. In a preferred embodiment, cells are isolated from the subject mammalian organism, transfected with a target nucleic acid (i.e., protease or PE-like proprotein nucleic acid), and re-infused back into the subject organism (e.g., patient). Various mammalian cell types suitable for ex vivo transfection are well known to those of skill in the art (see, e.g., Freshney et al., *Culture of Animal Cells, a Manual of Basic Technique,* third edition Wiley-Liss, New York (1994)) and the references cited therein for a discussion of how to isolate and culture cells from patients).

As indicated above, in a preferred embodiment, the packageable nucleic acid which encodes a target nucleic acid is under the control of an activated or constitutive promoter. The transfected cell(s) express functional PE-like proprotein or protease. In one particularly preferred embodiment, stem cells are used in ex vivo procedures for gene therapy. The advantage to using stem cells is that they can be differentiated into other cell types ex vivo, or can be introduced into a mammal (such as the donor of the cells) where they will engraft in the bone marrow. Methods for differentiating $CD34^+$ cells ex vivo into clinically important immune cell types using cytokines such a GM-CSF, IFN-γand TNF-αare known (see, Inaba et al. (1992) *J. Exp. Med.* 176, 1693–1702, and Szabolcs et al. (1995) 154: 5851–5861).

Stem cells are isolated for transfection and differentiation using known methods. For example, in mice, bone marrow cells are isolated by sacrificing the mouse and cutting the leg bones with a pair of scissors. Stem cells are isolated from bone marrow cells by panning the bone marrow cells with antibodies which bind unwanted cells, such as $CD4^+$ and $CD8^+$ (T cells), $CD45^+$ (panB cells), GR-1 (granulocytes), and $Ia^d$ (differentiated antigen presenting cells). For an example of this protocol see, Inaba et al. (1992) *J. Exp. Med.* 176, 1693–1702.

In humans, bone marrow aspirations from iliac crests are performed e.g., under general anesthesia in the operating room. The bone marrow aspirations is approximately 1,000 ml in quantity and is collected from the posterior iliac bones and crests. If the total number of cells collected is less than about $2 \times 10^8$/kg, a second aspiration using the sternum and anterior iliac crests in addition to posterior crests is performed. During the operation, two units of irradiated packed red cells are administered to replace the volume of marrow taken by the aspiration. Human hematopoietic progenitor and stem cells are characterized by the presence of a CD34 surface membrane antigen. This antigen is used for purification, e.g., on affinity columns which bind CD34. After the bone marrow is harvested, the mononuclear cells are separated from the other components by means of ficol gradient centrifugation. This is performed by a semi-automated method using a cell separator (e.g., a Baxter Fenwal CS3000+ or Terumo machine). The light density cells, composed mostly of mononuclear cells are collected and the cells are incubated in plastic flasks at 37° C. for 1.5 hours. The adherent cells (monocytes, macrophages and B-Cells) are discarded. The non-adherent cells are then collected and incubated with a monoclonal anti-CD34 antibody (e.g., the murine antibody 9C5) at 4° C. for 30 minutes with gentle rotation. Th final concentration for the anti-CD34 antibody is 10 μg/ml. After two washes, paramagnetic microspheres (Dyna Beads, supplied by Baxter Immunotherapy Group, Santa Ana, Calif.) coated with sheep anti-mouse IgG (Fc) antibody are added to the cell suspension at a ratio of 2 cells/bead. After a further incubation period of 30 minutes at 4° C., the rosetted cells with magnetic beads are collected with a magnet. Chymopapain (supplied by Baxter Immunotherapy Group, Santa Ana, Calif.) at a final concentration of 200 U/ml is added to release the beads from the CD34+ cells. Alternatively, and preferably, an affinity column isolation procedure can be used which binds to CD34, or to antibodies bound to CD34 (see, the examples below). See, Ho et al. (1995) *Stem Cells* 13 (suppl. 3): 100–105. See also, Brenner (1993) *Journal of Hematotherapy* 2: 7–17.

In another embodiment, hematopoetic stem cells are isolated from fetal cord blood. Yu et al. (1995) *Proc. Natl. Acad. Sci. USA,* 92: 699–703 describe a preferred method of transducing CD34$^+$ cells from human fetal cord blood using retroviral vectors.

VI. Pharmaceutical Compositions and Administration

The PE-like proprotein compositions of this invention, including PE-like proproteins and targeted PE-like proproteins (i.e., PE-like proprotein attached to a cell specific ligand), are particularly useful for parenteral administration, such as intravenous administration or administration into a body cavity or lumen of an organ. The compositions for administration will commonly comprise a solution of the PE molecule fusion protein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

The compositions containing the present fusion proteins or a cocktail thereof (i.e., with other proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose should be sufficient to treat or ameliorate symptoms or signs of disease without producing unacceptable toxicity to the patient. An effective amount of the compound is that which provides either subjective relief of a symptom(s) or an objectively identifiable improvement as noted by the clinician or other qualified observer.

Controlled release parenteral formulations of the PE-like protein compositions of the present invention can be made as implants, oily injections, or as particulate systems. For a broad overview of protein delivery systems see, Banga, A. J., "Therapeutic Peptides and Proteins: Formulation, Processing, and Delivery Systems" Technomic Publishing Company, Inc. 1995. Lancaster, Pa., incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J. 1994. "Nanoparticles," in *Colloidal Drug Delivery Systems,* J. Kreuter, ed., Marcel Dekker, Inc., New York, N.Y., pp. 219–342; Tice and Tabibi. 1992. "Parenteral Drug Delivery: Injectibles," in *Treatise on Controlled Drug Delivery,* A. Kydonieus, ed., Marcel Dekker, Inc. New York, N.Y., pp.315–339, both of which are incorporated herein by reference. Numerous systems for controlled delivery of therapeutic proteins are known. See, e.g., U.S. Pat. Nos. 5,055,303, 5,188,837, 4,235,871, 4,501,728, 4,837,028, 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Polymers are typically used for use ion controlled release of PE compositions of the present invention. Various degradable and nondegradable polymeric matrices for use in controlled drug delivery are known in the art. Langer, R. 1993. "Polymer-Controlled Drug Delivery Systems," *Accounts*

Chem. Res., 26:537–542. For example, the block copolymer, polaxamer 407 exists as a mobile viscous at low temperatures but forms a semisolid gel at body temperature. It has shown to be an efficacious vehicle for formulation and sustained delivery of recombinant interleukin-2 and urease. Johnston et al., Pharm. Res., 9:425–434 (1992); Pec et al., J. Parent. Sci. Tech., 44(2):58–65 (1990). Hydroxyapatite can also be used as a microcarrier for controlled release of proteins. Ijntema et al., Int. J. Pharm., 112:215–224 (1994). Liposomes can be used for controlled release as well as drug targeting of entrapped drug. Betageri et al. 1993. "Targeting of Liposomes," in Liposome Drug Delivery Systems, Technomic Publishing Co., Inc., Lancaster, Pa. See also, U.S. Pat. Nos. 4,235,871, 4,501,728, 4,837,028 4,957,735 and 5,019, 369, each of which is incorporated herein by reference.

PE-like proproteins are useful in the therapeutic treatment of subjects to kill cells that produce proteases that cleave a protease activatable sequence. More specifically, certain cancers can be treated in this way. This includes the treatment of prostate cancer, breast cancer or colon cancer. PE-like proproteins for treatment of prostate cancer comprise a PSA activatable sequence. A number of metastatically active cancers express urokinase. Accordingly, treatment of these cancers is generally by the use of a PE-like proprotein comprising a urokinase activatable sequence. Treatment involves administering the therapeutically effective dose of the preparation to the subject.

The following examples are offered by way of illustration, not by way of limitation.

EXAMPLES

I. Introduction

In this study, it was shown that protein engineering strategies can be used to alter the susceptibility of a recombinant immuntoxin to proteolytic processing. The furin-specific processing site of a PE-based immunotoxin was altered to render it cleavable by the cancer-expressed protease, PSA. Making toxin cleavage and activation a cancer-related event, achieves a second level of specificity for immunotoxin targeting. The altered immunotoxins were refractory to furin, and they exhibited toxicity toward a variety of non-PSA secreting cell lines. Thus, other proteases, not yet identified, can process these novel proteins.

Normally, cleavage of PE by furin occurs intracellularly. However, because the sessile bond is located within a portion of domain II that is stably held together by the disulfide bond that links cysteines 265 and 287, there is no requirement for cleavage to occur at an intracellular location. PSA cleavage and activation of the sem 1 and 2 immunotoxins could occur pericellularly, with the expectation that the cleaved immunotoxin would be robust enough to bind and enter cells and translocate to the cytosol. This was confirmed by experiments showing that in vitro cleavage by PSA produced nicked sem 1 and 2 immunotoxins that were very potent cytotoxic agents.

Figure 3:
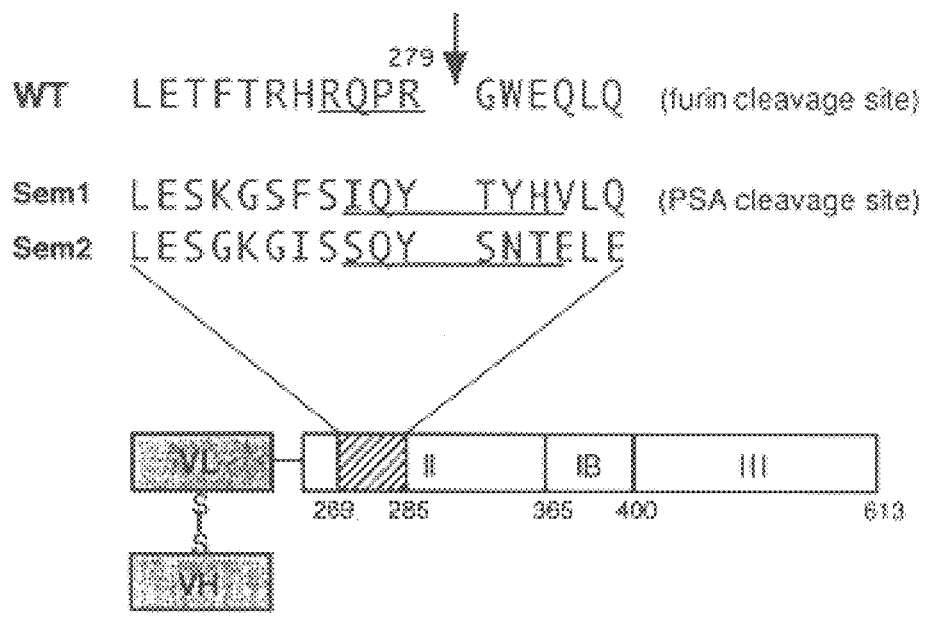
Figure 3:
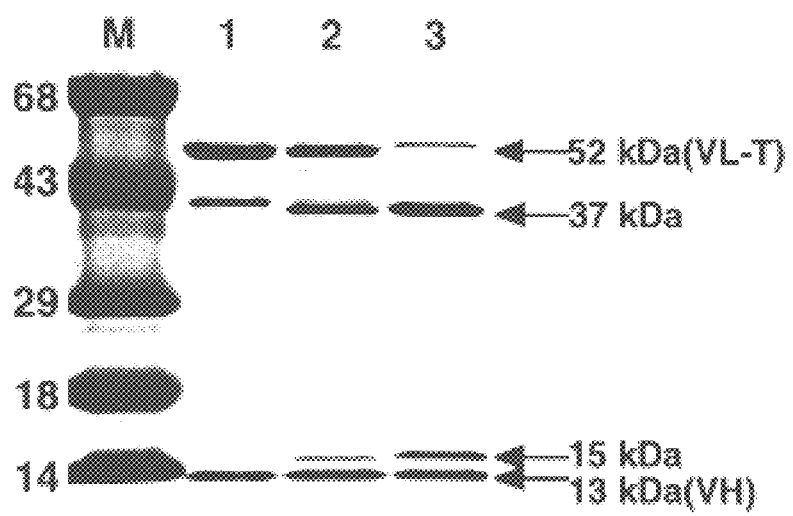

II. Construction of Plasmids for Expression of Recombinant Immunotoxins Containing Potential PSA Substrates To create a PE-derived immunotoxin that could be cleaved and activated by PSA, we made extensive alterations in the amino acid composition at the existing furin site. First, to eliminate furin cleavage, sequences between residues 273 and 284 in domain II of a PE-encoding plasmid, pMOA1A2VK352, were removed by excising a unique BspMI-XhoI fragment. This fragment was then replaced by oligonucleotide duplexes encoding potential substrate sequences for PSA. Specifically, the duplexes encoded amino acids 58–71 (sem1) or 151–163 (sem2) of semenogelin I (FIG. 3A). Finally, in a series of subcloning steps these inserts were transferred from the PE-encoding vector into a newly constructed disulfide stabilized Fv immunotoxin. As proof of concept, the PSA substrate sequences were inserted into an immunotoxin, HB21dsFvPE40, targeted to the human transferrin receptor.

Several design features should be noted. First, oligonucleotide duplexes were inserted to encode exactly the same number of amino acids that had been excised by digesting with BspMI and XhoI. Secondly, the P1 amino acid of each semenogelin sequence (which was tyrosine for both inserts) was inserted in the location normally occupied by the P1 arginine residue in the native sequence. Thirdly, inserts were chosen primarily to allow for cleavage by PSA.

Figure 2:
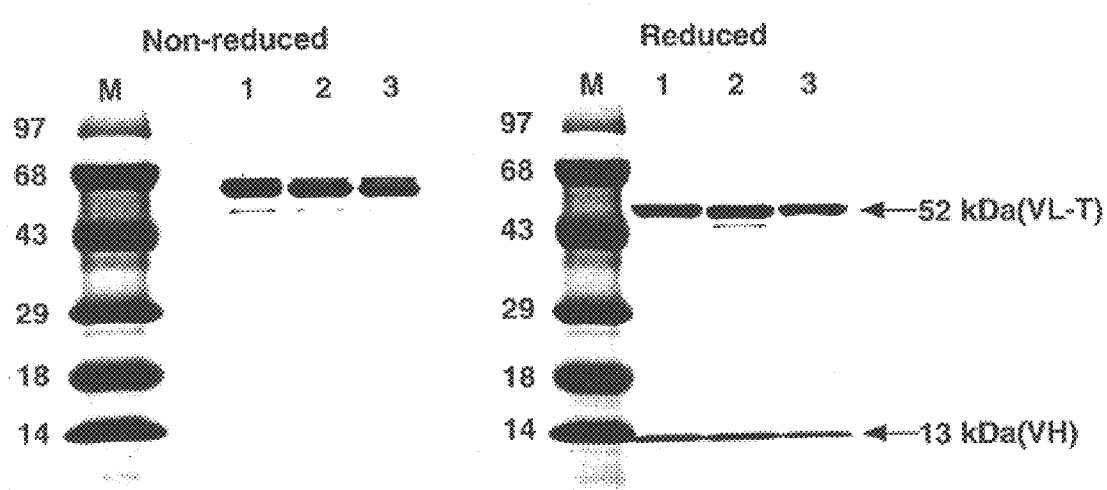

Components of the HB21dsFvPE40 immunotoxins (VH and VL-toxin), were expressed in separate E. coli BL21 (1DE3) cultures, recovered from inclusion bodies, and refolded as described herein. Refolded dsFv-immunotoxins were purified by Q-sepharose and mono-Q ion exchange chromatography using established protocols for dsFv-immunotoxin purification (Reiter et al., Biochemistry, pp. 5451–5459, 1994 #115; Buchner Anal. Biochem. 205, pp. 263–270 (1992), #113). Yields of purified, active, recombinant toxins after mono-Q chromatography ranged from 10–20% of total protein refolded. SDS-PAGE analysis revealed that recombinant immunotoxins were >90% pure (FIG. 2).

Expression plasmids encoding the components of the disulfide-stabilized immunotoxin, HB21(dsFv)PE38K (pPWHB38K and pPWHBVH) were constructed through site-directed mutagenesis (Kunkel et al., 1993) and subcloning as shown in FIG. 1. Uracil-containing single-stranded DNA of the plasmid pRKHB9K, encoding HB21(scFv) PE38K (Kreitman, 1997) was used as template DNA. Three mutagenic oligonucleotides were used for making pPWHBVH, encoding HB21VH(cys). 5' GTTGAAGCCA GAAGCCTTGC AGGACAACTG AC 3' (SEQ ID NO:14), deleted the HindIII site at position 151 for cloning purposes; 5' CCATCCAATC CACTCTAGAC ACTGTTCAGG CCTCTG 3' (SEQ ID NO:15) replaced gly45 with cysteine; and 5' GCCGCCACCA CCGGATC<u>GAA TTC</u>ATTATGA GGAGACGGTG AC 3' (SEQ ID NO:16) introduced a stop codon followed by an EcoRI site at the 3' end of the anti-transferrin VH gene. Each oligo contained an analytical restriction site (underlined) for identification of positive clones. To make pPWHB38K, encoding HB2VL(cys) PE38K, an NdeI site and ATG translation initiation codon were introduced at the 5' end of the anti-transferrin VL gene using the oligonucleotide 5' GGTCATTACA ATATT <u>CATATG</u>GCCACCT CCAGAGCC 3' (SEQ ID NO:17). Ala238 was mutated to cysteine using the oligonucleotide 5' ATCTCCAGCT <u>TGGTACC</u>ACA ACGAACGTGA GAGG 3' (SEQ ID NO:18). Clones containing all three mutations for making expression plasmid pPWHBVH were selected for through restriction analysis with newly introduced or deleted restriction sites, HindIII, EcoRI, and XbaI.

Clones containing both mutations for making pPWHBPE38K were selected for through restriction analysis with NdeI and Asp718. pPWHBVH was subsequently constructed by deleting an EcoRI fragment encoding the linker and HB21VL(cys)PE38K. pPWHB38K was constructed by deleting an NdeI fragment encoding HB21VH (cys) and the linker. Correct pPWHBVH and pPWHB38K clones were identified by restriction analysis and confirmed by DNA sequencing.

Expression plasmids pPWHB40sem1 and pPWHB40sem2 encoding HB21VL(cys)PE40(sem1) and HB21VL(cys)PE40(sem2), respectively, were constructed as shown in FIG. 1. Oligonucleotide duplexes containing semenogelin I sequences were each inserted into pMOA 1A1VK352, encoding whole PE (Ogata, et al., 1992), between BspMI(937) and XhoI (981) sites to create pPW-MOsem1 and pPWMOsem2. Oligonucleotide Sem1(5' GGAGTCAAAA GGAAGCTTTT CAATTCAATA CACATATCAT GTAC 3') (SEQ ID NO:19), encoding PSA substrate IQYTYH (SEQ ID NO:20) along with flanking sequences, contained a HindIII analytical restriction site (underlined). Oligonucleotide Sem2, 5' GGAGTCAGGA AAAGGTATTT CATCTCAGTA CTCAAATACA GAAC 3' (SEQ ID NO:21), encoding PSA substrate SQYSNT (SEQ ID NO:22) and flanking sequences, contained a ScaI restriction site. Positive clones were selected for through the presence of the new restriction sites. To construct final expression plasmids pPWHB40(sem1) and pPWHB40 (sem2), a 1.129 kb BspMI/EcoRI fragment encoding PE40 and inserted semenogelin sequences was subcloned from pPWMOsem1 and 2 into pPWHB38K. Positive pPWHB40sem1 and pPWHB40sem2 clones were identified by restriction analysis with EcoRI/XhoI, BamHI, or ScaI/XbaI, respectively.

Control expression plasmid, pPWHB40, encoding HB21VL(cys)PE40(wt), was constructed by subcloning a 1.2 kb HindIII/EcoRI fragment encoding PE40 and an intact furin cleavage site from pRK78, which encodes anti-Tac (Fv)PE40 (Spence et al, *Bioconj. Chem.* 4, (1993)), into HindIII/EcoRI digested pPWHB38K. Positive clones were identified through restriction analysis.

III. Protein Expression and Purification

The HB21dsFvPE40 immunotoxins were produced as two separate components, VH and VL-toxin. HB21VL(cys) PE40(sem), HB21VL(cys)PE40(wt), and HB21VH(cys) proteins were expressed in separate *E. coli* BL21 DE3 cultures containing the corresponding expression plasmid. Cells were grown in Superbroth (Advanced Biotechnologies Inc.) supplemented with 100 μg/ml Ampicillin, 1.62 mM MgSO$_4$, and 0.4% glucose at 37° C., from a starting A600 of 0.2 to A600=3.0. Protein expression was induced with isopropyl-β-D-thiogalactopyranoside (IPTG) at 1 mM for 1.5 hours. Bacterial cells were pelleted and lysed with 200 μg/ml lysozyme in 50 mM Tris (pH 7.4), 20 mM EDTA (pH 8.0). Insoluble inclusion bodies containing the recombinant proteins were purified, solubilized (6M Guanidine-HCl, 0.1 M Tris (pH 8.0), 2 mM EDTA), and reduced with dithierythritol (DTE) (pH 8.0–8.5) at 65 mM for 4 hrs at RT, as described previously (Buchner et al., 1992). Solubilized, reduced IB proteins were combined in a 2:1 molar ratio of VH to VL-toxin and diluted 100-fold into redox-shuffling renaturation buffer (0.1 M Tris, 0.5 M L-Arginine-HCl, 0.9 mM glutathione, 2 mM EDTA, pH 9.5) (Brinkmann et al., *Proc. Nat'l. Acad. Sci. U.S.A.* 90, pp. 7538–7542, (1993B); Buchner et al., 1992). Refolding mix was incubated at 10° C. for 36–40 hours and dialyzed against 20 mM Tris (pH 7.4), 100 mM Urea until conductivity was reduced to 2.5–3.0 mMHO. Properly folded immunotoxins were purified byion-exchange on Q-Sepharose and MonoQ columns.

IV. PSA Cleavage Assays

Figure 4:
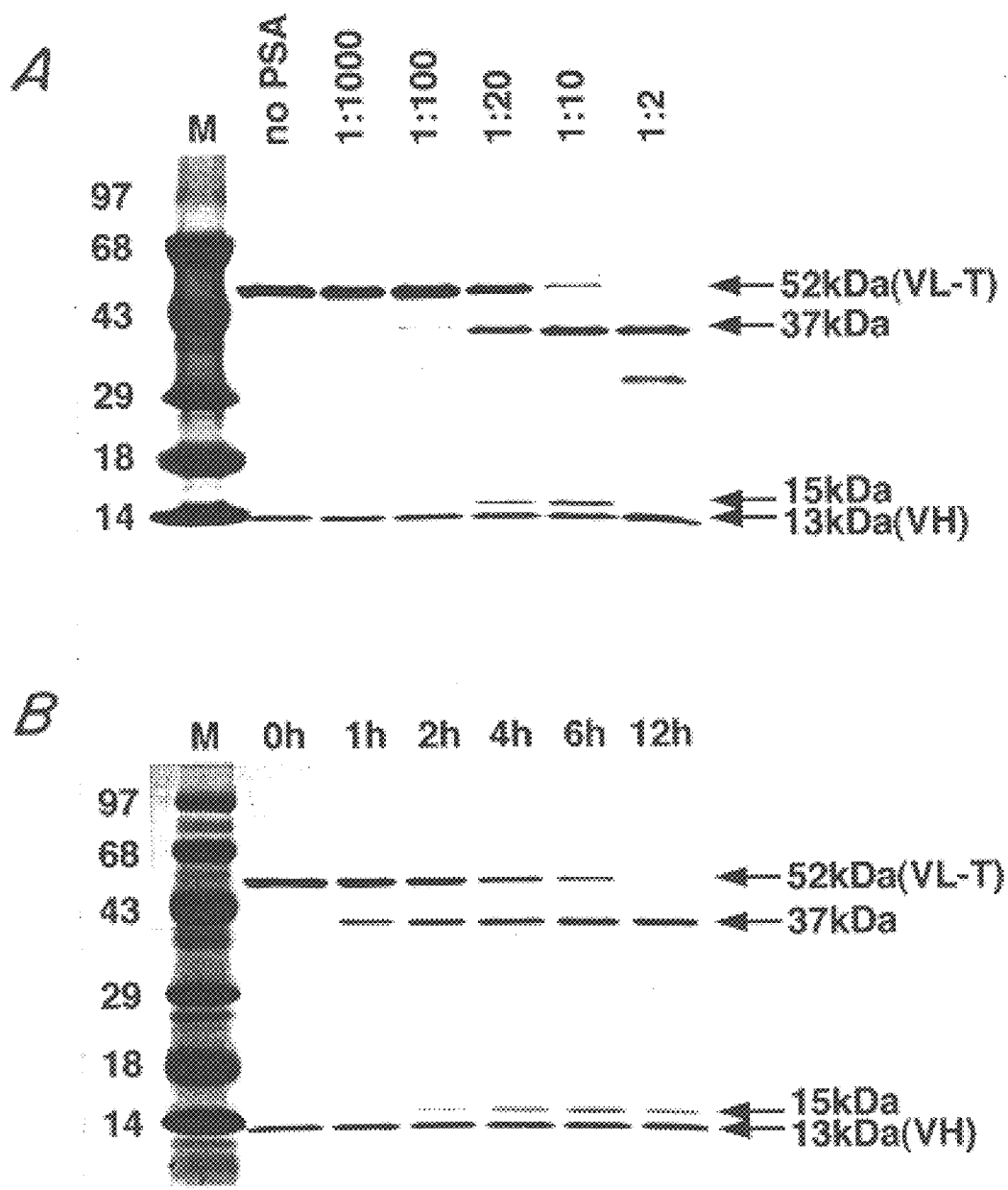

To test the susceptibility of HB21dsFvPE40 immunotoxins to cleavage by PSA, we incubated HB21dsFvPE40(wt) and HB21dsFvPE40(sem1 and 2) with varying amounts of enzymatically active PSA in 50 Tris, 100 mM NaCl (pH 7.0) at 37° C. Cleavage conditions were first optimized by testing different incubation periods (FIG. 4A), various enzyme to substrate ratios (FIG. 4B), and various pH conditions. Cleavage products were analyzed by SDS-PAGE and Coomassie Blue staining. Optimal conditions for producing the desired cleavage products with a minimal amount of non-specific cleavage were 6 hours of incubation with PSA at a 1:10 molar ratio of enzyme to substrate at 37° C., pH 7.0.

Enzymatically active PSA was purchased from Fitzgerald Industries International, Inc (Concord, Mass.). For PSA cleavage assays, immunotoxins were incubated with PSA in PSA Buffer (50 mM Tris, 100 mM NaCl, pH 7.0) at 37° C. For time course reactions, 20 μg HB21(sem2)dsFvPE40 was diluted in 100 μl of PSA Buffer to a final concentration of 3 uM. PSA was added to a final concentration of 0.3 μM for an enzyme: substrate molar ratio of 1:10. Twenty μl aliquots were taken at 0, 1, 3, 6, and 12 hr time points, and reactions were stopped with reducing SDS-PAGE sample buffer. Reduced samples were run on 4–20 % SDS-PAGE gradient gels to analyze the extent of cleavage by PSA. For enzyme-:substrate ratio assays, 4 ug of HB21dsFvPE40(sem2) was incubated with PSA at various concentrations for 6 hours at 37° C. Reactions were stopped with reducing SDS-PAGE sample buffer and analyzed through SDS-PAGE.

As shown (FIG. 3B, lane 3), HB21dsFvPE40(sem2) was more susceptible to cleavage than the semi version (lane 2). Using the above conditions, approximately 90% of the sem2 immunotoxin was cleaved to produce fragments of 37 kD and 15 kD while only ~20% of HB21dsFvPE40(sem1) was cleaved (FIG. 3B, lane 2). PSA cleaved the sem 1 and 2 immunotoxins at only one site. At very high PSA to immunotoxin ratios with long incubation times there was a minor cleavage product when the wt immunotoxin was incubated with PSA (FIG. 3B, lane 1 and below). N-terminal sequence analysis of the 37 kD carboxy-terminal fragments confirmed that cleavage had occurred between tyrosine and serine in sem2 and tyrosine and threonine in sem1. These are the same peptide bonds that are cleaved in semenogelin I by PSA. The incubation of HB21dsFvPE40-wt with high concentrations of PSA produced a minor fragment (FIG. 3B, lane 1) that migrated slower than the 37 kD fragment generated from the HB21dsFvPE40(sem1 and 2) immunotoxins. When this fragment was sequenced, it indicated that cleavage had occurred between threonine 260 and alanine 261 of PE.

V. Amino Terminus Sequencing of PSA Cleavage Products

Fifty μg of whole PE and recombinant immunotoxins HB21dsFvPE40(sem1) and HB21dsFvPE40(sem2) were each incubated with 7.7 μg PSA (10:1 molar ratio) in 75 μl PSA Buffer at 37° C. for 6 hours. Reactions were stopped with 25 μl reducing sample buffer, and cleavage products were separated on 4–20% SDS-PAGE gels. Proteins were transferred to Immobilon-P transfer membrane (Millipore), and the 37 kD cleavage product was excised and sequenced by Edman degradation (Bowman Gray School of Medicine, Winston-Salem, N.C).

VI. Furin Cleavage Assay

Furin cleaves substrates having basic residues (most often arginines) at positions P1, P2 and P4 (Hosaka, 1991 #24). The presence of proline at P2 is also well tolerated (Matthews, 1994 #119; Chiron et al., (1994) *J. Biol. Chem.* 269:18167–18176.). To determine whether or not the sem1 and 2 immunotoxins were susceptibile to furin-mediated cleavage, we incubated them with furin at a 1:10 molar ratio for 16 hours at 25° C.

Furin was prepared as described (Chiron, et al., 1993). Four μg of recombinant immunotoxins were each incubated with 485 μg furin (1:10 enzyme: substrate molar ratio) in furin buffer (0.2 M NaOAc (pH 5.5), 5 mM CaCl2) for 16 hours at room temperature. These conditions were previously established as optimal for furin cleavage of PE (Chiron, et al., 1993). Reactions were stopped with reducing sample buffer, and samples were run on 4–20% SDS-PAGE gradient gels.

SDS-PAGE analysis of the reaction mixture indicated that the sem1 and 2 immunotoxins were indeed refractory to furin (FIG. 5). The wildtype immunotoxin was cleaved, and products were of the expected sizes, 15 kD (N-terminal fragment) and 37 kD (C-terminal fragment).

VII. Cleavage by Other Serine Proteases

PSA has been described as a serine protease with chymotrypsin-like specificity. It was therefore of interest to determine whether or not the changes that rendered sem1 and 2 immunotoxins susceptible to PSA, made them more susceptible to other serine proteases. WT, sem1 and 2 immunotoxins were each incubated with urokinase or with sequencing grade trypsin or chymotrypsin and the products analyzed by reducing and non-reducing SDS-PAGE. Results indicated that the sem1 and 2 immunotoxins were cleaved by these proteases. However, compared to the WT immunotoxin there was no evidence of increased susceptibility to any of these three proteases.

VIII. Cytotoxicity Assays

Activity of HB21dsFvPE40(wt) and HB21dsFvPE40 (sem) immunotoxins was determined by inhibition of protein synthesis in cultured cells, as previously described (Brinkmann et al, 1991). In assays using immunotoxins pre-cleaved by PSA, immunotoxins were incubated with PSA at a 1:10 molar ratio for 6 hours at 37° C. before being added to cells. For competition experiments, mAb HB21 or mAb OVB3 was added 15 minutes before the addition of immunotoxins.

Previous characterizations of prostate cancer cell lines have indicated that LnCAP cells express PSA while DU145 cells do not. It was therefore of interest to evaluate the relative cytotoxic activity of the sem1 and 2 immunotoxins on both these lines. In an overnight assay on LnCap cells, the sem2 immuotoxin was 10-fold more active than the sem1 immunotoxin (Table 1). This correlated with its greater susceptibility to cleavage by PSA.

Figure 6A:
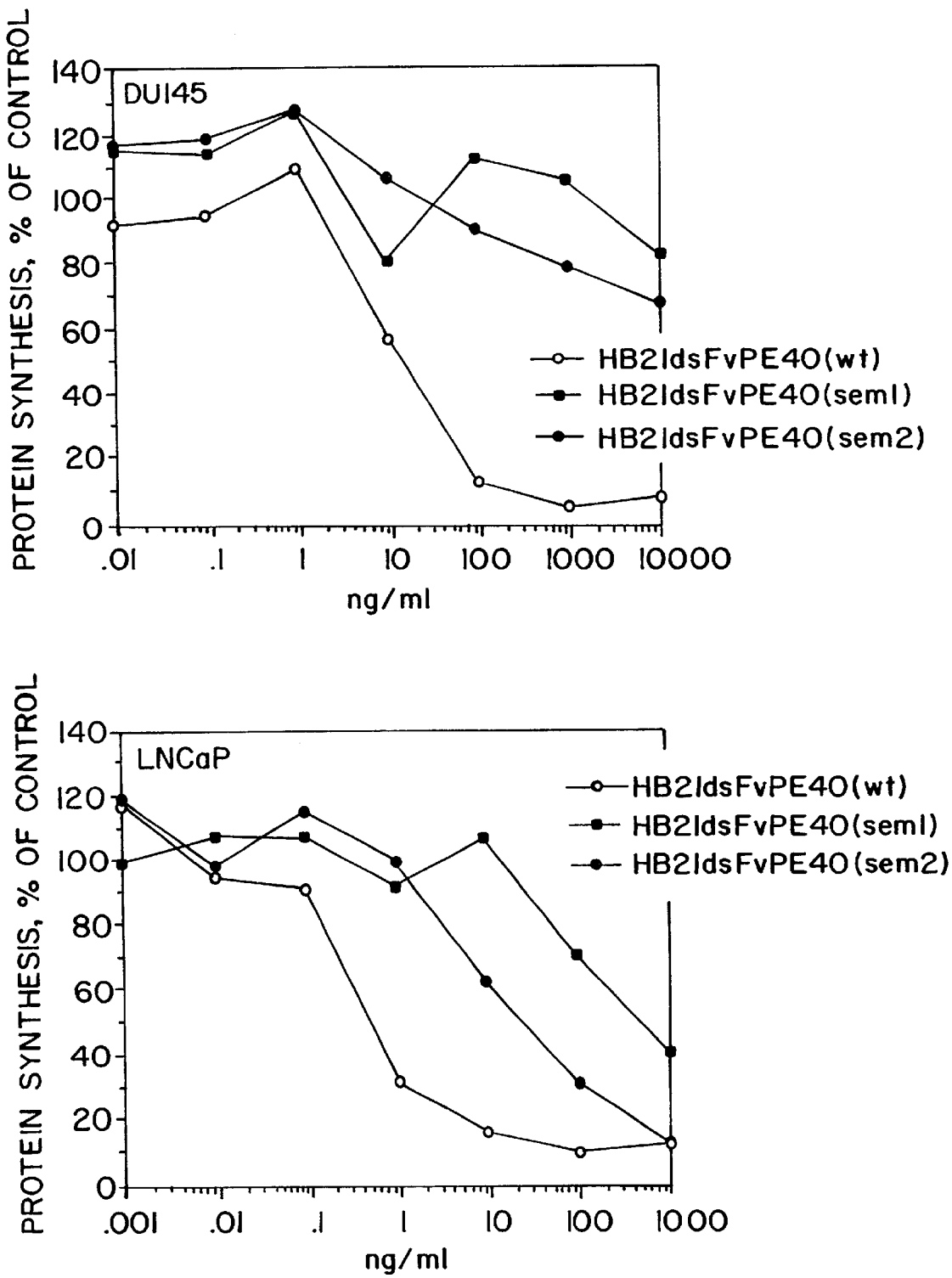
Figure 6B:
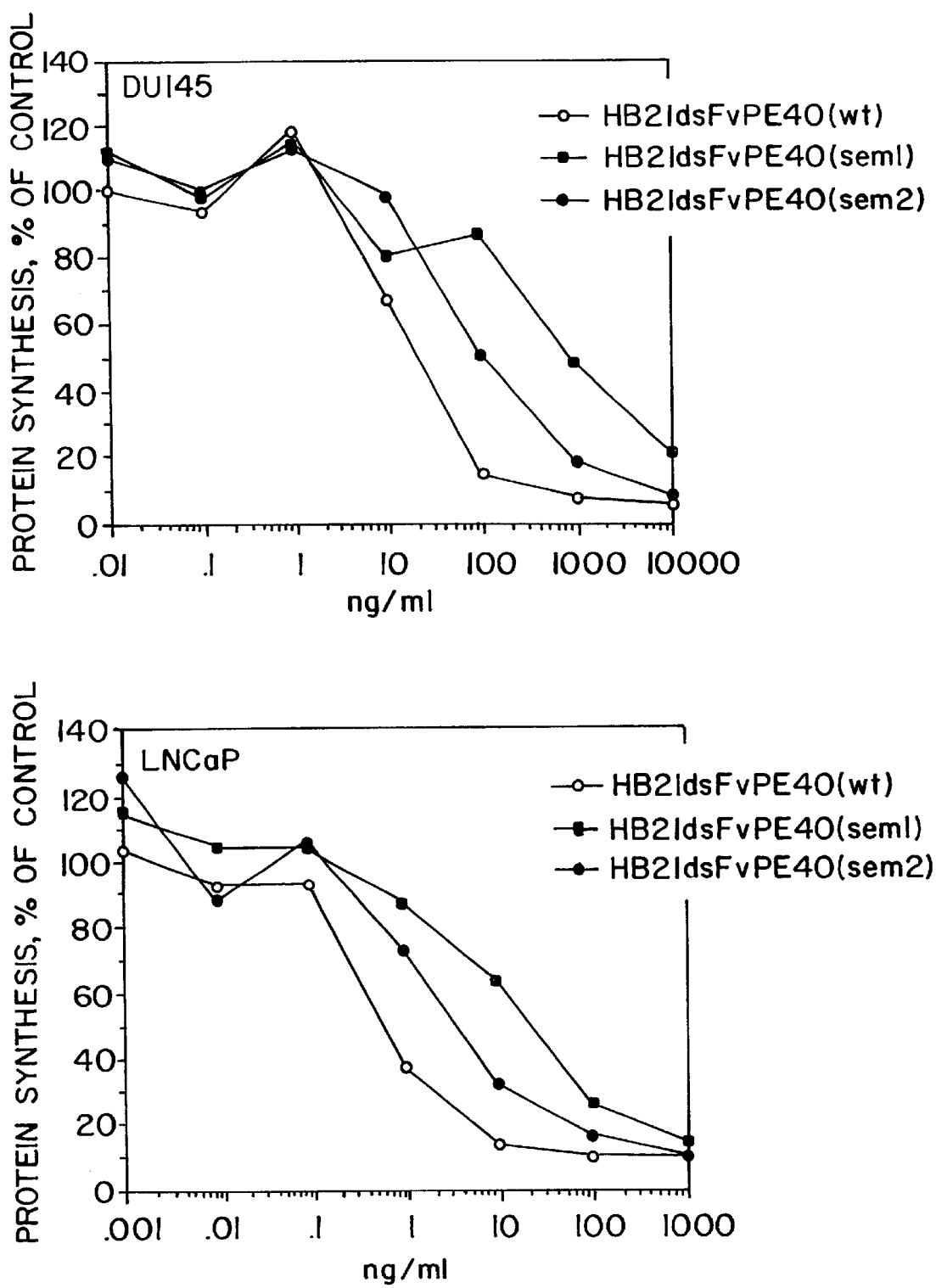
Figure 8:
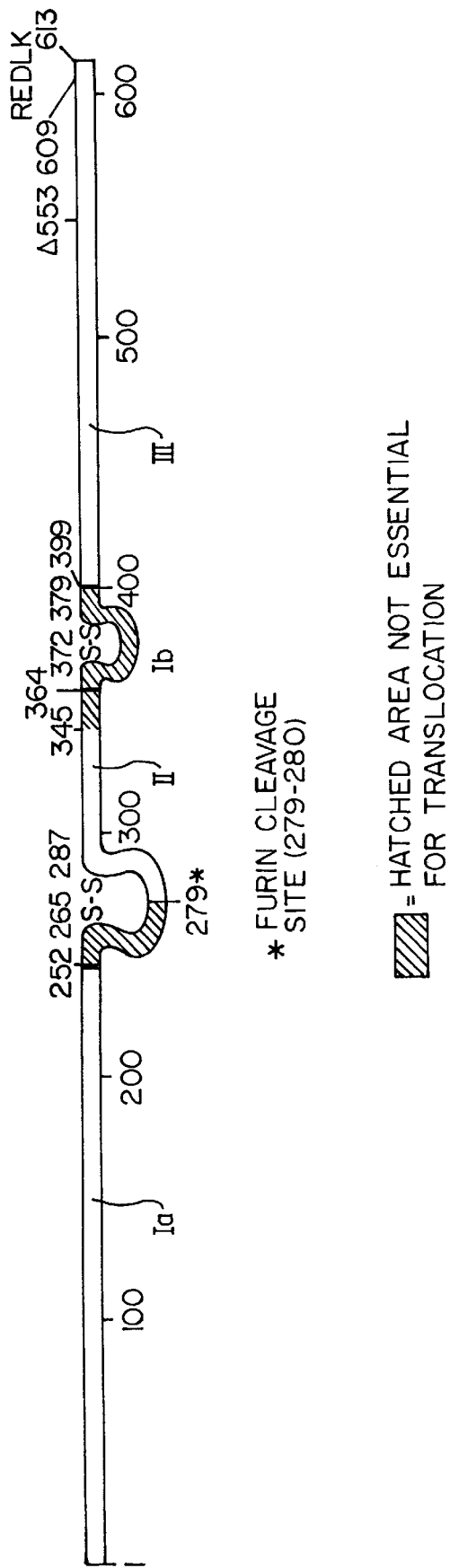
Figure 9:
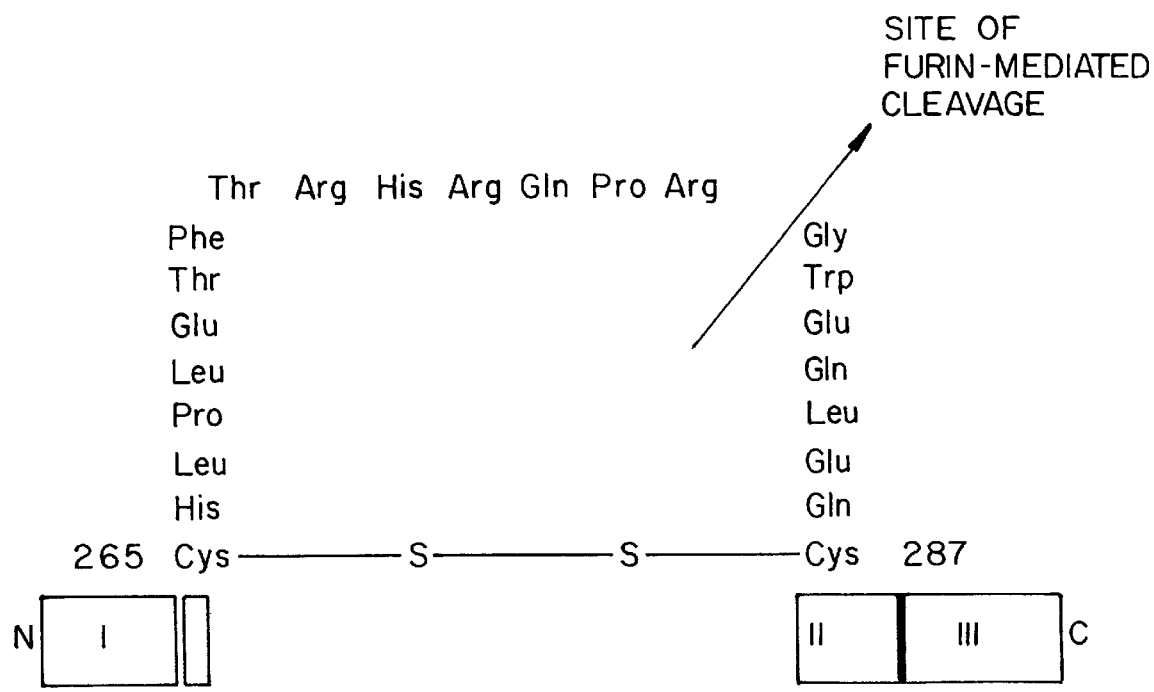

Because of the presence of protease inhibitors in serum-containing tissue culure media, the proteolytic activity of PSA was not easy to evaluate. Therefore, additional experiments were undertaken. Sem 1 and 2 immunotoxins were first incubated with PSA in vitro and the resulting nicked toxins added to cells for 4 hr. In these short term assays, precleavage by PSA dramatically increased the potency of the sem 1 and 2 immuntoxins. PSA cleavage reduced the $IC_{50}$ of sem 1 from 500 ng/ml to 25 ng/ml while the $IC_{50}$ of sem 2 went from 25 to 3.7 ng/ml (FIG. 6A and B). Without knowing the proteolytic activity contributed by cell-associated PSA, these values probably represent the optimal activity of the sem1 and 2 immuntoxins. Under these conditions the precleaved sem2 immuntoxin was only 6-fold less potent than the WT immunotoxin (see below and discussion).

Unexpectedly, the sem 1 and 2 immunotoxins were also toxic for DU145 cells with the sem 2 immunotoxin being 5-fold more active than the sem1 version (Table 1). Since DU145 cells are not known to secrete PSA, this suggested that other proteases could also process the immuntoxins. In addition to PSA, prostate cancer cells express other kallikreins, cathespsin D and may convert pro-urokinase to its active form. Further study will determine the proteolytic activity associated with these cells.

The result with the DU145 cells prompted the evaluatation of the cytotoxic activity of the sem 1 and 2 immuntoxins on a variety of non-prostate cell lines. In constrast to the results on LnCAP and DU145, there was no differential between the activity of the sem 1 and 2 immunotoxins when they were assayed on HUT-102, A431, MCF-7 and OVCAR-3 cells (Table 1).

On all cell lines tested, the sem1 and 2 immunotoxins were less active than the WT immunotoxin. This reduction may be due to differences in the ability of the 37 kD cleavage product to translocate to the cell cytosol rather than differences in proteolytic processing. On the prostate lines, the sem2 immunotoxin was 50-fold less active than WT while on non-prostate cells the difference ranged from 4-fold for HUT-102 cells to 600-fold for MCF-7.

These studies reveal that sem1 and 2 immunotoxins were cytotoxic on a variety of cell lines. However, their potencey was reduced compared to the wild-type immunotoxin. This reduction is probably due to differences in the ability of the 37 kD C-terminal fragment to translocate to the cell cytosol. In native PE, tryptophan 280 and leucine 284 at the N-terminus of the 37 kD fragment appear to be important for translocation to the cytosol. In our sem 1 and 2 immunotoxins, we inserted 13–15 new amino acids and consequently, altered 3–4 residues on the P' side of the sessile bond. These residues may not mediate translocation as efficiently as the wild-type $NH_2$ terminal GWEQLE sequence (SEQ ID NO:36).

IX. Stability Assays

To confirm binding specificity, it was shown that excess HB21 antibody blocked the cytotoxic activity of HB21dsFvPE40 (sem2), while the addition of a similar concentration of an irrelevant antibody, OVB3, failed to block activity. Because, in constructing the sem1 and 2 immunotoxins, a substantial number of amino acids in PE40 were altered, it was important to determine whether protein stability had been altered. This was also important because the sem 1 and 2 immunotoxins were less active than the WT immunotoxin. The stability of HB21dsFvPE40(wt) and HB21dsFvPE40(sem2) was assayed by incubating each immunotoxin at 10 μg/ml in human serum at 37° C. Active immunotoxin remaining after various incubation periods was determined by 20 hr cytotoxicity assays on cultured cells. No reduction was noted compared to a sample that had been stored frozen.

TABLE 1

Cytotoxic activity of WT, Sem1 and 2 immunotoxins on various human cancer cell lines.

| Cell line (tissue) | Immunotoxin | $IC_{50}$ (ng/ml) |
| --- | --- | --- |
| LnCAP (prostate ca) | WT | 0.03 |
|  | sem1 | 20 |
|  | sem2 | 3.0 |
| DU145 (prostate ca) | WT | 0.5 |
|  | sem1 | 80 |
|  | sem2 | 25 |
| A431 (epidermoid ca) | WT | 0.005 |
|  | sem1 | 2.0 |
|  | sem2 | 2.0 |
| HUT-102 (T-leukemia) | WT | 0.5 |
|  | sem1 | 2.0 |
|  | sem2 | 3.0 |
| MCF-7 (breast ca) | WT | 0.005 |
|  | sem1 | 4.0 |
|  | sem2 | 3.0 |
| OVCAR-3 (ovarian ca) | WT | 1.5 |
|  | sem1 | 35 |
|  | sem2 | 20 |

X. Urokinase-Activatable Sequence

To cleave its substrates, furin requires an arginine residue at postions P1 and P4, as defined above. Urokinase cleaves substrates when there are arginines at both P1 and P2. Immunotoxins with a wtPE sequence between residues 272 and 284 are cleaved by furin but not by uPA. Diphtheria toxin is cleaved by furin and uPA. To construct a sequence resembling the loop of DT, eight amino acids were inserted—where these replaced the wtPE sequences, they are underlined. The new immunotoxin is cleaved both by furin and by uPA. To render this immunotoxin resistant to furin and susceptible to uPA, additional mutants were made. Only the change of arginine to alanine allowed for the production a stable protein that was cleaved by uPA and not by furin (changes to glycine and glutamine did not produce a useful mutant).

Residues to the right of the cleavage site are called the P' amino acids. P'2 in wtPE is tryptophan. The presence of tryptophan in this location is very important for the toxicity of wtPE and PE-derived immunotoxins. To construct and immunotoxin that has a tryptophan at P'2 and is cleavable by uPA, an additional set of variants were generated. Among these was the restoration of tryptophan at the P'2 position. This mutation retained the distinction of being cleaved by uPA and not by furin. In cell experiments the presence of tryptophan at the P'2 position proved to be most cytotoxic when proteins were cleaved by uPA and then added to target cells (see graphs).

The present invention provides Pseudomonas exotoxin A-like proproteins and methods of using them. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A protease-activatable Pseudomonas exotoxin A-like ("PE-like") proprotein comprising:
    (a) a cell recognition domain that binds to an exterior surface of a targeted cell;
    (b) a modified PE translocation domain comprising an amino acid sequence with 80% or greater sequence identity to amino acids 280 to 344 of SEQ ID NO:2 and which effects translocation to a cell cytosol upon proteolytic cleavage, wherein the translocation domain comprises a cysteine-cysteine loop that comprises a protease activatable sequence cleavable by a protease and wherein the protease activatable sequence is refractory to cleavage by furin when incubated with furin at a 1:10 enzyme:substrate molar ratio at 25° C. for 16 hour;

(c) a cytotoxicity domain comprising an amino acid sequence with 80% or greater sequence identity to amino acids 400 to 613 of SEQ ID NO:2, the cytotoxicity domain having ADP-ribosylating activity; and (d) an endoplasmic reticulum ("ER") retention sequence.

2. The PE-like proprotein of claim 1 wherein the modified PE translocation domain has a PE domain II sequence (amino acids 253–364 of SEQ ID NO:1) modified with amino acids substitutions introducing the protease activatable sequence so as to cause cleavage by the protease between amino acids 279 and 280.

3. The PE-like proprotein of claim 1 wherein the protease activatable sequence is cleavable by a protease secreted by a cancer cell.

4. The PE-like proprotein of claim 1 wherein the cell recognition domain comprises an antibody that specifically binds to a cancer cell surface marker.

5. The PE-like proprotein of claim 2 wherein the protease activatable sequence is cleavable by prostate specific antigen ("PSA").

6. The PE-like proprotein of claim 2 wherein the protease activatable sequence is cleavable by urokinase.

7. The PE-like proprotein of claim 2 wherein the protease activatable sequence is cleavable by neutral endoprotease, stromelysin, collagenase, cathepsin B, or cathepsin D.

8. The PE-like proprotein of claim 2 further comprising a PE Ib domain, and wherein said PE Ib domain, the cytotoxicity domain, and the ER retention sequence together have the sequence of domains Ib and III of native PE.

9. The PE-like proprotein of claim 3 wherein the cell recognition domain is coupled to the modified translocation domain through a peptide bond.

10. The PE-like proprotein of claim 5 wherein the protease activatable sequence is SKGSFSIQYTYHV (SEQ ID NO:11), HLGGSQQLLHNKQ (SEQ ID NO:12), or SKGKGTSSQYSNTE (SEQ ID NO:13).

11. The PE-like proprotein of claim 6 wherein the protease activatable sequence is DRVYIHPF (SEQ ID NO:3), VVCGERGFFYTP (SEQ ID NO:4), FFYTPKA (SEQ ID NO:5), KRRPVKVYP (SEQ ID NO:6), PVGKKRRPVKVY (SEQ ID NO:7), KPVGKKRRPVKV (SEQ ID NO:8), GKPVGKKRRPVK (SEQ ID NO:9), or TFAGNAVRRSVGQ (SEQ ID NO:10).

12. The PE-like proprotein of claim 8 wherein the cell recognition domain is an antibody coupled to the modified translocation domain through a peptide bond and wherein the antibody specifically binds a cancer cell surface marker.

13. A composition comprising a pharmaceutically acceptable carrier and a therapeutically effective amount of a protease-specific Pseudomonas exotoxin A-like ("PE-like") proprotein comprising:

(a) a cell recognition domain that binds to an exterior surface of a targeted cell;

(b) a modified PE translocation domain comprising an amino acid sequence with 80% or greater sequence identity to amino acids 280 to 344 of SEQ ID NO:2 and which effects translocation to a cell cytosol upon proteolytic cleavage, wherein the translocation domain comprises a cysteine-cysteine loop that comprises a protease activatable sequence cleavable by a protease and wherein the protease activatable sequence is substantially un-activatable by fibrin when incubated with furin at a 1:10 enzyme:substrate molar ratio at 25° C. for 16 hours;

(c) a cytotoxicity domain comprising an amino acid sequence with 80% or greater sequence identity to amino acids 400 to 613 of SEQ WD NO:2, the cytotoxicity domain having ADP-ribosylating activity; and (d) an endoplasmic reticulum ("ER") retention sequence.

14. The composition of claim 13, further comprising a PE Ib-like domain, wherein:

(a) the cell recognition domain is an antibody coupled to the modified PE translocation domain through a peptide bond and wherein the antibody specifically binds a cancer cell surface marker;

(b) the modified PE translocation domain has a PE domain II sequence (amino acids 253–364 of SEQ ID NO:1) modified with amino acids substitutions introducing the protease activatable sequence so as to cause cleavage by the protease between amino acids 279 and 280; and (c) the PE Ib-like domain, the cytotoxicity domain and the ER retention sequence together have the sequence of domains Ib and III of native PE.

15. The composition of claim 14 wherein the protease activatable sequence is cleavable by prostate specific antigen or urokinase.

16. A method for killing a cancer cell comprising contacting the cell with a protease-specific Pseudomonas exotoxin A-like ("PE-like") proprotein comprising:

(a) a cell recognition domain that binds to an exterior surface of a targeted cell;

(b) a modified PE translocation domain comprising an amino acid sequence with 80% or greater sequence identity to amino acids 280 to 344 of SEQ ID NO:2 and which effects translocation to a cell cytosol upon proteolytic cleavage, wherein the translocation domain comprises a cysteine-cysteine loop that comprises a protease activatable sequence cleavable by a protease and wherein the protease activatable sequence cysteine-cysteine loop is substantially un-activatable by furin when incubated with furin at a 1:10 enzyme:substrate molar ratio at 25° C. for 16 hours;

(c) a cytotoxicity domain comprising an amino acid sequence with 80% or greater sequence identity to amino acids 400 to 613 of SEQ ID NO:2, the cytotoxicity domain having ADP-ribosylating activity; and (d) an endoplasmic reticulum ("ER") retention sequence.

17. The method of claim 16 wherein the cancer cell is a prostate cancer cell.

18. The method of claim 16 wherein the cancer cell is a colon cancer cell.

19. The method of claim 16 used in the treatment of a subject suffering from cancer.

* * * * *

SEQUENCE LISTING (1) GENERAL INFORMATION:

(iii) NUMBER OF SEQUENCES: 36

(2) INFORMATION FOR SEQ ID NO:1:

(i) SEQUENCE CHARACTERISTICS:
      (A) LENGTH: 1839 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1839
      (D) OTHER INFORMATION: /product= "Pseudomonas exotoxin A"

(xi) SEQUENCE DESCRIPTION: SEQ ID NO:1:

```
GCC GAA GAA GCT TTC GAC CTC TGG AAC GAA TGC GCC AAA GCC TGC GTG        48
Ala Glu Glu Ala Phe Asp Leu Trp Asn Glu Cys Ala Lys Ala Cys Val
 1               5                  10                  15

CTC GAC CTC AAG GAC GGC GTG CGT TCC AGC CGC ATG AGC GTC GAC CCG        96
Leu Asp Leu Lys Asp Gly Val Arg Ser Ser Arg Met Ser Val Asp Pro
                20                  25                  30

GCC ATC GCC GAC ACC AAC GGC CAG GGC GTG CTG CAC TAC TCC ATG GTC       144
Ala Ile Ala Asp Thr Asn Gly Gln Gly Val Leu His Tyr Ser Met Val
            35                  40                  45

CTG GAG GGC GGC AAC GAC GCG CTC AAG CTG GCC ATC GAC AAC GCC CTC       192
Leu Glu Gly Gly Asn Asp Ala Leu Lys Leu Ala Ile Asp Asn Ala Leu
        50                  55                  60

AGC ATC ACC AGC GAC GGC CTG ACC ATC CGC CTC GAA GGC GGC GTC GAG       240
Ser Ile Thr Ser Asp Gly Leu Thr Ile Arg Leu Glu Gly Gly Val Glu
 65                  70                  75                  80

CCG AAC AAG CCG GTG CGC TAC AGC TAC ACG CGC CAG GCG CGC GGC AGT       288
Pro Asn Lys Pro Val Arg Tyr Ser Tyr Thr Arg Gln Ala Arg Gly Ser
                 85                  90                  95

TGG TCG CTG AAC TGG CTG GTA CCG ATC GGC CAC GAG AAG CCC TCG AAC       336
Trp Ser Leu Asn Trp Leu Val Pro Ile Gly His Glu Lys Pro Ser Asn
                100                 105                 110

ATC AAG GTG TTC ATC CAC GAA CTG AAC GCC GGC AAC CAG CTC AGC CAC       384
Ile Lys Val Phe Ile His Glu Leu Asn Ala Gly Asn Gln Leu Ser His
```

-continued

|   |   |   |   | 115 |   |   |   | 120 |   |   |   | 125 |   |   |     |
|---|---|---|---|-----|---|---|---|-----|---|---|---|-----|---|---|-----|
| ATG | TCG | CCG | ATC | TAC | ACC | ATC | GAG | ATG | GGC | GAC | GAG | TTG | CTG | GCG | AAG | 432 |
| Met | Ser | Pro | Ile | Tyr | Thr | Ile | Glu | Met | Gly | Asp | Glu | Leu | Leu | Ala | Lys |     |
| 130 |     |     |     |     | 135 |     |     |     |     | 140 |     |     |     |     |     |     |

```
CTG GCG CGC GAT GCC ACC TTC TTC GTC AGG GCG CAC GAG AGC AAC GAG      480
Leu Ala Arg Asp Ala Thr Phe Phe Val Arg Ala His Glu Ser Asn Glu
145             150                 155                 160

ATG CAG CCG ACG CTC GCC ATC AGC CAT GCC GGG GTC AGC GTG GTC ATG      528
Met Gln Pro Thr Leu Ala Ile Ser His Ala Gly Val Ser Val Val Met
                165                 170                 175

GCC CAG ACC CAG CCG CGC CGG GAA AAG CGC TGG AGC GAA TGG GCC AGC      576
Ala Gln Thr Gln Pro Arg Arg Glu Lys Arg Trp Ser Glu Trp Ala Ser
                180                 185                 190

GGC AAG GTG TTG TGC CTG CTC GAC CCG CTG GAC GGG GTC TAC AAC TAC      624
Gly Lys Val Leu Cys Leu Leu Asp Pro Leu Asp Gly Val Tyr Asn Tyr
            195                 200                 205

CTC GCC CAG CAA CGC TGC AAC CTC GAC GAT ACC TGG GAA GGC AAG ATC      672
Leu Ala Gln Gln Arg Cys Asn Leu Asp Asp Thr Trp Glu Gly Lys Ile
        210                 215                 220

TAC CGG GTG CTC GCC GGC AAC CCG GCG AAG CAT GAC CTG GAC ATC AAA      720
Tyr Arg Val Leu Ala Gly Asn Pro Ala Lys His Asp Leu Asp Ile Lys
225                 230                 235                 240

CCC ACG GTC ATC AGT CAT CGC CTG CAC TTT CCC GAG GGC GGC AGC CTG      768
Pro Thr Val Ile Ser His Arg Leu His Phe Pro Glu Gly Gly Ser Leu
                245                 250                 255

GCC GCG CTG ACC GCG CAC CAG GCT TGC CAC CTG CCG CTG GAG ACT TTC      816
Ala Ala Leu Thr Ala His Gln Ala Cys His Leu Pro Leu Glu Thr Phe
                260                 265                 270

ACC CGT CAT CGC CAG CCG CGC GGC TGG GAA CAA CTG GAG CAG TGC GGC      864
Thr Arg His Arg Gln Pro Arg Gly Trp Glu Gln Leu Glu Gln Cys Gly
            275                 280                 285

TAT CCG GTG CAG CGG CTG GTC GCC CTC TAC CTG GCG GCG CGG CTG TCG      912
Tyr Pro Val Gln Arg Leu Val Ala Leu Tyr Leu Ala Ala Arg Leu Ser
        290                 295                 300

TGG AAC CAG GTC GAC CAG GTG ATC CGC AAC GCC CTG GCC AGC CCC GGC      960
Trp Asn Gln Val Asp Gln Val Ile Arg Asn Ala Leu Ala Ser Pro Gly
305                 310                 315                 320

AGC GGC GGC GAC CTG GGC GAA GCG ATC CGC GAG CAG CCG GAG CAG GCC     1008
Ser Gly Gly Asp Leu Gly Glu Ala Ile Arg Glu Gln Pro Glu Gln Ala
                325                 330                 335

CGT CTG GCC CTG ACC CTG GCC GCC GCC GAG AGC GAG CGC TTC GTC CGG     1056
Arg Leu Ala Leu Thr Leu Ala Ala Ala Glu Ser Glu Arg Phe Val Arg
                340                 345                 350

CAG GGC ACC GGC AAC GAC GAG GCC GGC GCG GCC AAC GCC GAC GTG GTG     1104
Gln Gly Thr Gly Asn Asp Glu Ala Gly Ala Ala Asn Ala Asp Val Val
            355                 360                 365

AGC CTG ACC TGC CCG GTC GCC GCC GGT GAA TGC GCG GGC CCG GCG GAC     1152
Ser Leu Thr Cys Pro Val Ala Ala Gly Glu Cys Ala Gly Pro Ala Asp
        370                 375                 380

AGC GGC GAC GCC CTG CTG GAG CGC AAC TAT CCC ACT GGC GCG GAG TTC     1200
Ser Gly Asp Ala Leu Leu Glu Arg Asn Tyr Pro Thr Gly Ala Glu Phe
385                 390                 395                 400

CTC GGC GAC GGC GGC GAC GTC AGC TTC AGC ACC CGC GGC ACG CAG AAC     1248
Leu Gly Asp Gly Gly Asp Val Ser Phe Ser Thr Arg Gly Thr Gln Asn
                405                 410                 415

TGG ACG GTG GAG CGG CTG CTC CAG GCG CAC CGC CAA CTG GAG GAG CGC     1296
Trp Thr Val Glu Arg Leu Leu Gln Ala His Arg Gln Leu Glu Glu Arg
                420                 425                 430

GGC TAT GTG TTC GTC GGC TAC CAC GGC ACC TTC CTC GAA GCG GCG CAA     1344
```

```
Gly Tyr Val Phe Val Gly Tyr His Gly Thr Phe Leu Glu Ala Ala Gln
            435                 440                 445

AGC ATC GTC TTC GGC GGG GTG CGC GCG CGC AGC CAG GAC CTC GAC GCG      1392
Ser Ile Val Phe Gly Gly Val Arg Ala Arg Ser Gln Asp Leu Asp Ala
        450                 455                 460

ATC TGG CGC GGT TTC TAT ATC GCC GGC GAT CCG GCG CTG GCC TAC GGC      1440
Ile Trp Arg Gly Phe Tyr Ile Ala Gly Asp Pro Ala Leu Ala Tyr Gly
465                 470                 475                 480

TAC GCC CAG GAC CAG GAA CCC GAC GCA CGC GGC CGG ATC CGC AAC GGT      1488
Tyr Ala Gln Asp Gln Glu Pro Asp Ala Arg Gly Arg Ile Arg Asn Gly
                485                 490                 495

GCC CTG CTG CGG GTC TAT GTG CCG CGC TCG AGC CTG CCG GGC TTC TAC      1536
Ala Leu Leu Arg Val Tyr Val Pro Arg Ser Ser Leu Pro Gly Phe Tyr
            500                 505                 510

CGC ACC AGC CTG ACC CTG GCC GCG CCG GAG GCG GCG GGC GAG GTC GAA      1584
Arg Thr Ser Leu Thr Leu Ala Ala Pro Glu Ala Ala Gly Glu Val Glu
        515                 520                 525

CGG CTG ATC GGC CAT CCG CTG CCG CTG CGC CTG GAC GCC ATC ACC GGC      1632
Arg Leu Ile Gly His Pro Leu Pro Leu Arg Leu Asp Ala Ile Thr Gly
    530                 535                 540

CCC GAG GAG GAA GGC GGG CGC CTG GAG ACC ATT CTC GGC TGG CCG CTG      1680
Pro Glu Glu Glu Gly Gly Arg Leu Glu Thr Ile Leu Gly Trp Pro Leu
545                 550                 555                 560

GCC GAG CGC ACC GTG GTG ATT CCC TCG GCG ATC CCC ACC GAC CCG CGC      1728
Ala Glu Arg Thr Val Val Ile Pro Ser Ala Ile Pro Thr Asp Pro Arg
                565                 570                 575

AAC GTC GGC GGC GAC CTC GAC CCG TCC AGC ATC CCC GAC AAG GAA CAG      1776
Asn Val Gly Gly Asp Leu Asp Pro Ser Ser Ile Pro Asp Lys Glu Gln
            580                 585                 590

GCG ATC AGC GCC CTG CCG GAC TAC GCC AGC CAG CCC GGC AAA CCG CCG      1824
Ala Ile Ser Ala Leu Pro Asp Tyr Ala Ser Gln Pro Gly Lys Pro Pro
        595                 600                 605

CGC GAG GAC CTG AAG                                                  1839
Arg Glu Asp Leu Lys
    610

(2) INFORMATION FOR SEQ ID NO:2:

(i) SEQUENCE CHARACTERISTICS:
        (A) LENGTH: 613 amino acids
        (B) TYPE: amino acid
        (D) TOPOLOGY: linear (ii) MOLECULE TYPE: protein (xi) SEQUENCE DESCRIPTION: SEQ ID NO:2:

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110
```

```
Ile Lys Val Phe Ile His Glu Leu Asn Ala Gly Asn Gln Leu Ser His
        115                 120                 125
Met Ser Pro Ile Tyr Thr Ile Glu Met Gly Asp Glu Leu Leu Ala Lys
        130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Thr Gln Pro Arg Arg Glu Lys Arg Trp Ser Glu Trp Ala Ser
                180                 185                 190
Gly Lys Val Leu Cys Leu Leu Asp Pro Leu Asp Gly Val Tyr Asn Tyr
                195                 200                 205
Leu Ala Gln Gln Arg Cys Asn Leu Asp Asp Thr Trp Glu Gly Lys Ile
210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                245                 250                 255
Ala Ala Leu Thr Ala His Gln Ala Cys His Leu Pro Leu Glu Thr Phe
                260                 265                 270
Thr Arg His Arg Gln Pro Arg Gly Trp Glu Gln Leu Glu Gln Cys Gly
                275                 280                 285
Tyr Pro Val Gln Arg Leu Val Ala Leu Tyr Leu Ala Ala Arg Leu Ser
                290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
                325                 330                 335
Arg Leu Ala Leu Thr Leu Ala Ala Glu Ser Glu Arg Phe Val Arg
                340                 345                 350
Gln Gly Thr Gly Asn Asp Glu Ala Gly Ala Ala Asn Ala Asp Val Val
                355                 360                 365
Ser Leu Thr Cys Pro Val Ala Ala Gly Glu Cys Ala Gly Pro Ala Asp
        370                 375                 380
Ser Gly Asp Ala Leu Leu Glu Arg Asn Tyr Pro Thr Gly Ala Glu Phe
385                 390                 395                 400
Leu Gly Asp Gly Gly Asp Val Ser Phe Ser Thr Arg Gly Thr Gln Asn
                405                 410                 415
Trp Thr Val Glu Arg Leu Leu Gln Ala His Arg Gln Leu Glu Glu Arg
                420                 425                 430
Gly Tyr Val Phe Val Gly Tyr His Gly Thr Phe Leu Glu Ala Ala Gln
                435                 440                 445
Ser Ile Val Phe Gly Gly Val Arg Ala Arg Ser Gln Asp Leu Asp Ala
        450                 455                 460
Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
                485                 490                 495
Ala Leu Leu Arg Val Tyr Val Pro Arg Ser Ser Leu Pro Gly Phe Tyr
                500                 505                 510
Arg Thr Ser Leu Thr Leu Ala Ala Pro Glu Ala Ala Gly Glu Val Glu
        515                 520                 525
```

```
Arg Leu Ile Gly His Pro Leu Pro Leu Arg Leu Asp Ala Ile Thr Gly
    530                 535                 540
Pro Glu Glu Glu Gly Gly Arg Leu Glu Thr Ile Leu Gly Trp Pro Leu
545                 550                 555                 560
Ala Glu Arg Thr Val Val Ile Pro Ser Ala Ile Pro Thr Asp Pro Arg
                565                 570                 575
Asn Val Gly Gly Asp Leu Asp Pro Ser Ser Ile Pro Asp Lys Glu Gln
            580                 585                 590
Ala Ile Ser Ala Leu Pro Asp Tyr Ala Ser Gln Pro Gly Lys Pro Pro
        595                 600                 605
Arg Glu Asp Leu Lys
    610
```

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Asp Arg Val Tyr Ile His Pro Phe
1               5
```

(2) INFORMATION FOR SEQ ID NO:4:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Val Val Cys Gly Glu Arg Gly Phe Phe Tyr Thr Pro
1               5                   10
```

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Phe Phe Tyr Thr Pro Lys Ala
1               5
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Lys Arg Arg Pro Val Lys Val Tyr Pro
1               5
```

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Pro Val Gly Lys Lys Arg Arg Pro Val Lys Val Tyr
1               5                   10
```

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Lys Pro Val Gly Lys Lys Arg Arg Pro Val Lys Val
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Gly Lys Pro Val Gly Lys Lys Arg Arg Pro Val Lys
1               5                   10
```

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Thr Phe Ala Gly Asn Ala Val Arg Arg Ser Val Gly Gln
1               5                   10
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Ser Lys Gly Ser Phe Ser Ile Gln Tyr Thr Tyr His Val
1               5                   10

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

His Leu Gly Gly Ser Gln Gln Leu Leu His Asn Lys Gln
1               5                   10

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Ser Lys Gly Lys Gly Thr Ser Ser Gln Tyr Ser Asn Thr Glu
1               5                   10

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GTTGAAGCCA GAAGCCTTGC AGGACAACTG AC                                32

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

CCATCCAATC CACTCTAGAC ACTGTTCAGG CCTCTG                            36

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GCCGCCACCA CCGGATCGAA TTCATTATGA GGAGACGGTG AC                    42

(2) INFORMATION FOR SEQ ID NO:17:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GGTCATTACA ATATTCCATA TGGCCACCTC CAGAGCC                          37

(2) INFORMATION FOR SEQ ID NO:18:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

ATCTCCAGCT TGGTACCACA ACGAACGTGA GAGG                             34

(2) INFORMATION FOR SEQ ID NO:19:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..44
        (D) OTHER INFORMATION: /note= "oligonucleotide Sem1"

(xi) SEQUENCE DESCRIPTION: SEQ ID NO:19:

GGAGTCAAAA GGAAGCTTTT CAATTCAATA CACATATCAT GTAC                  44

(2) INFORMATION FOR SEQ ID NO:20:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

Ile Gln Tyr Thr Tyr His
1               5

(2) INFORMATION FOR SEQ ID NO:21:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA

```
    (ix) FEATURE:
         (A) NAME/KEY: -
         (B) LOCATION: 1..44
         (D) OTHER INFORMATION: /note= "oligonucleotide Sem2"

(xi) SEQUENCE DESCRIPTION: SEQ ID NO:21:

GGAGTCAGGA AAAGGTATTT CATCTCAGTA CTCAAATACA GAAC                    44

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Ser Gln Tyr Ser Asn Thr
1               5

(2) INFORMATION FOR SEQ ID NO:23:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Leu Glu Thr Phe Thr Arg His Arg Gln Pro Arg Gly Trp Glu Gln Leu
1               5                   10                  15

Gln (2) INFORMATION FOR SEQ ID NO:24:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Leu Glu Ser Lys Gly Ser Phe Ser Ile Gln Tyr Thr Tyr His Val Leu
1               5                   10                  15

Gln (2) INFORMATION FOR SEQ ID NO:25:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Leu Glu Ser Gly Lys Gly Ile Ser Ser Gln Tyr Ser Asn Thr Glu Leu
1               5                   10                  15

Glu
```

(2) INFORMATION FOR SEQ ID NO:26:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

```
Phe Thr Arg His Arg Gln Pro Arg Gly Trp Glu Gln Leu
1               5                   10
```

(2) INFORMATION FOR SEQ ID NO:27:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

```
Phe Ala Gly Asn Arg Val Arg Arg Ser Val Gly Gln Leu
1               5                   10
```

(2) INFORMATION FOR SEQ ID NO:28:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

```
Phe Ala Gly Asn Ala Val Arg Arg Ser Val Gly Gln Leu
1               5                   10
```

(2) INFORMATION FOR SEQ ID NO:29:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

```
Cys His Leu Pro Leu Glu Thr Phe Thr Arg His Arg Gln Pro Arg Gly
1               5                   10                  15
Trp Glu Gln Leu Glu Gln Cys
            20
```

(2) INFORMATION FOR SEQ ID NO:30:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

```
Arg Xaa Xaa Arg
1
```

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

```
Arg Gln Pro Arg Gly Trp Glu Gln
1               5
```

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

```
Ile Glu Gly Arg
1
```

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

```
Arg Glu Asp Leu Lys
1               5
```

(2) INFORMATION FOR SEQ ID NO:34:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

```
Arg Glu Asp Leu
1
```

(2) INFORMATION FOR SEQ ID NO:35:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide -continued

```
    (xi) SEQUENCE DESCRIPTION: SEQ ID NO:35:

Lys Asp Glu Leu
1

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Gly Trp Glu Gln Leu Glu
1               5
```